United States Patent
Faber et al.

(10) Patent No.: US 8,945,389 B2
(45) Date of Patent: Feb. 3, 2015

(54) METHOD FOR SUBSTANCE SEPARATION USING A CELLULOSE HYDRATE MEMBRANE IN SIZE EXCLUSION CHROMATOGRAPHY

(75) Inventors: René Faber, Göttingen (DE); Wolfgang Demmer, Göttingen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 993 days.

(21) Appl. No.: 12/937,899

(22) PCT Filed: Feb. 10, 2009

(86) PCT No.: PCT/EP2009/000915
§ 371 (c)(1),
(2), (4) Date: Feb. 10, 2011

(87) PCT Pub. No.: WO2009/127287
PCT Pub. Date: Oct. 22, 2009

(65) Prior Publication Data
US 2011/0163029 A1    Jul. 7, 2011

(30) Foreign Application Priority Data

Apr. 14, 2008   (DE) .......................... 10 2008 018 732

(51) Int. Cl.
*B01D 15/08*    (2006.01)
*B01D 71/10*    (2006.01)
(Continued)

(52) U.S. Cl.
CPC ............... *B01D 71/10* (2013.01); *B01D 15/34* (2013.01); *B01D 67/0093* (2013.01); *B01D 69/02* (2013.01); *B01J 20/28033* (2013.01);
(Continued)

(58) Field of Classification Search
None
See application file for complete search history.

(56) References Cited

U.S. PATENT DOCUMENTS

| 6,103,121 A | 8/2000 | Bhattacharyya et al. |
| 2004/0069707 A1* | 4/2004 | Naldrett ........................ 210/638 |

(Continued)

FOREIGN PATENT DOCUMENTS

| DE | 4323913 A1 | 1/1995 |
| DE | 10 2004 053 787 A1 | 5/2006 |

(Continued)

OTHER PUBLICATIONS

International Search Report dated May 27, 2009, for International Application No. PCT/EP2009/000915.

(Continued)

*Primary Examiner* — Allison Fitzsimmons
(74) *Attorney, Agent, or Firm* — Knobbe, Martens, Olson & Bear, LLP

(57) ABSTRACT

There is proposed a separation method for mixtures of materials, using a cellulose hydrate membrane having a porous double structure which consists of micropores having a diameter in the range from >100 nm to 20 μm and ultrapores which have a diameter of <100 nm and which are not accessible to Blue Dextran having an average molecular weight Mw of 2 000 000, wherein the fraction of the volume of the ultrapores is more than 15% of the entire pore volume accessible to water, and wherein, in a preferred embodiment, sulfonic acid ligands are bonded to the membrane.

23 Claims, 13 Drawing Sheets

Figure 1:
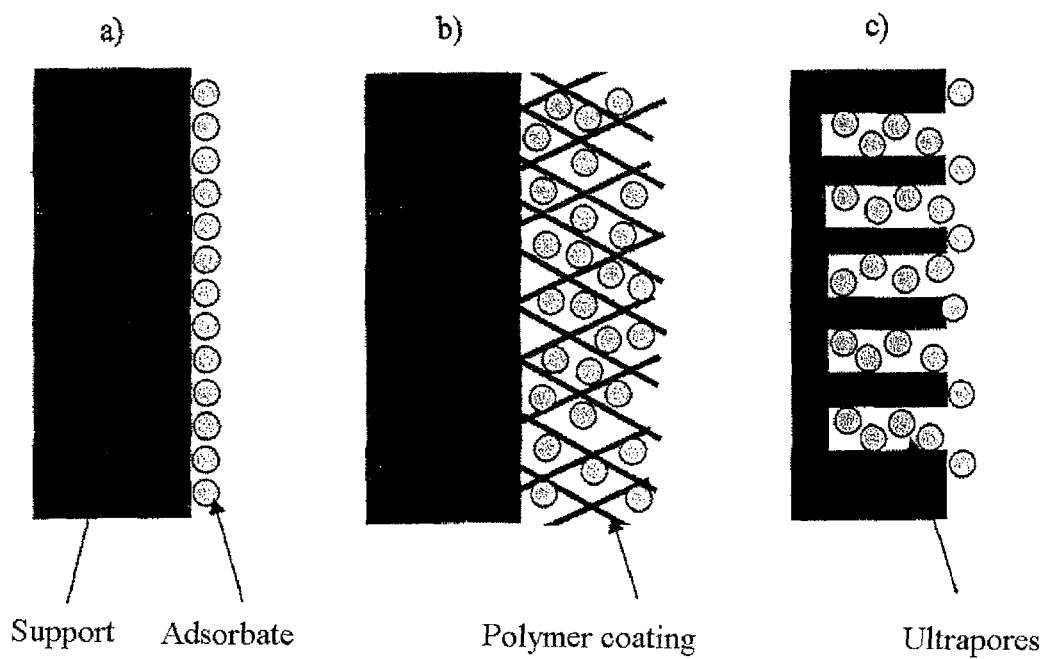

(51) Int. Cl.
  *B01D 15/34* (2006.01)
  *B01D 67/00* (2006.01)
  *B01D 69/02* (2006.01)
  *B01J 20/28* (2006.01)
  *C07K 1/22* (2006.01)
  *C07K 1/36* (2006.01)
  *C08B 1/08* (2006.01)
  *C08B 15/10* (2006.01)
  *B01D 69/06* (2006.01)

(52) U.S. Cl.
  CPC ...... *B01J20/28035* (2013.01); *B01J 20/28078* (2013.01); *C07K 1/22* (2013.01); *C07K 1/36* (2013.01); *C08B 1/08* (2013.01); *C08B 15/10* (2013.01); *B01D 2323/16* (2013.01); *B01D 2323/30* (2013.01); *B01D 2323/36* (2013.01); *B01D 2325/02* (2013.01); *B01D 2325/12* (2013.01); *B01D 2325/14* (2013.01); *B01D 2325/16* (2013.01)
  USPC ........... 210/638; 210/656; 210/660; 210/767; 210/500.1; 210/500.27; 210/502.1; 210/508

(56) References Cited

U.S. PATENT DOCUMENTS

2007/0244307 A1    10/2007    Engstrand
2008/0179248 A1    7/2008     Axen

FOREIGN PATENT DOCUMENTS

| EP | 0586268 B1 | 2/2000 |
| WO | WO 03/015902 A2 | 2/2003 |
| WO | WO 2007/017085 A2 | 2/2007 |
| WO | WO 2008/095709 A1 | 8/2008 |

OTHER PUBLICATIONS

Hermanson, et al., "Immobilized Affinity Ligand Techniques", Academic Press, Inc., San Diego, 1992, in 104 pages. (Duo to the large file size, this document is divided and filed in three separate parts).

* cited by examiner

Lysozyme bound to the adsorptively active polymer layer

Membrane-penetrating micropores

Coarse structure of relatively thick fibers of the cellulose or their agglomerates, adsorptively inactive More finely distributed fibroid or clusterlike membrane material Membrane-penetrating micropores Coarse structure of relatively thick fibers of the cellulose or their agglomerates, with bound lysozyme More finely distributed fibroid or clusterlike membrane material, with bound lysozyme Membrane-penetrating micropores Coarse structure of relatively thick fibers of the cellulose or their agglomerates with ultrapores accessible to biomolecules, with bound lysozyme More finely distributed fibroid or clusterlike membrane material with ultrapores accessible to biomolecules, with bound lysozyme

METHOD FOR SUBSTANCE SEPARATION USING A CELLULOSE HYDRATE MEMBRANE IN SIZE EXCLUSION CHROMATOGRAPHY

This application is the U.S. National Phase of International Application No. PCT/EP2009/000915, filed Feb. 10, 2009, designating the U.S. and published in German as WO 2009/127287 on Oct. 22, 2009 which claims the benefit of German Patent Application No. 10 2008 018 732.1, filed Apr. 14, 2008.

The present invention relates to a method for material separation in liquid media by virtue of a combination of an adsorptive interaction of the adsorbate with the adsorbent and of the size-exclusion effect. More particularly, the present invention relates to a method which uses a combination of membrane chromatography and size-exclusion chromatography for material separation.

Physical separation methods, in which material separation occurs through distribution between a stationary and a mobile phase, is known by the term chromatography. The equilibrium can form owing to different physicochemical effects.

When the distribution is achieved through adsorption to a solid (adsorbent) as a stationary phase, this is known as adsorption chromatography, e.g., ion-exchange chromatography, affinity chromatography, and hydrophobic interaction chromatography.

Gel-permeation chromatography (GPC) is a type of liquid chromatography. However, the separation here takes place owing exclusively to the size (more precisely: the hydrodynamic volume) of the molecules in solution. A further name is size-exclusion chromatography (SEC). When an aqueous eluting agent is used, the term gel filtration or gel-filtration chromatography (GFC) is also commonly used.

Filtration is understood to mean a method for separating solid particles or molecules from liquids (e.g., suspensions, protein solutions) or from gases (e.g., dust), even insoluble liquid droplets from another liquid (emulsion) or from gases (aerosols). A common, essential feature of filtration is that a porous medium (e.g., filter paper, membrane) is perfused by the continuous phase (liquid or gas), with the solid particles, molecules, or droplets being retained (retention) at the same time on the surface of the porous medium or inside.

Porous membranes are used mainly in the methods of ultrafiltration, of microfiltration, and of dialysis. Whether a particle or molecule is retained by ultrafiltration membranes or microfiltration membranes depends, in addition to the operating conditions, in particular on its size and structure relative to the size and structure of the membrane pores. A typical area of use of microfiltration is, for example, the concentration of suspensions, whereas ultrafiltration is often used for fractionating dissolved low-molecular-weight materials and macromolecules. A complete separation with ultrafiltration requires in this context that the molecular weights of the materials to be fractionated differ by at least one order of magnitude.

The pore size of microfiltration membranes is in the micrometer range (from about 0.08 to about 10 µm). The pore size of ultrafiltration membranes is mostly defined by specifying the limit at which 90% (or 95%) of the molecules of a particular molar mass are retained (molecular weight cutoff, MWCO).

Selectivity of a membrane is understood to mean its ability to distinguish between the components of a mixture.

Adsorptive membranes, also referred to as membrane adsorbers, are known in the prior art. To bring about purely adsorptive separation, mostly microfiltration membranes are modified with functional groups (ligands). Performing chromatographic separations with the help of adsorption membranes is also referred to as membrane chromatography, and all of the synthetic and natural ligands known in chromatography can also be used in the same way for adsorption membranes. The flat adsorbent consists mostly of one or more layers of an adsorptive membrane. Since filtration effects with the adsorptive membranes are rather undesired, the pore sizes of the adsorptive membranes used on an industrial scale are mostly in the range of >0.4 µm. Owing to this pore size, such membranes show mostly only a weak dependence of protein binding on protein size.

The binding of the adsorbates to the adsorbent can be reversible or irreversible; in any case, it makes possible their separation from the fluids, which are generally aqueous liquids and referred to hereinafter as media. The term "elution" summarizes the desorption and the accompanying rinse steps, and the liquid used for elution is the "eluent". The components can represent one or more target substances and/or one or more contaminants. "Target substances" are valuable materials which are to be recovered in an enriched or pure form from the medium. "Contaminants" are materials whose absence is required or desirable for technical, regulatory, or other reasons. For the removal of contaminants, which is referred to as "negative adsorption", the adsorption can (may) proceed irreversibly when the adsorbent is to be used only once. In the case of adsorption of target substance(s), the process must proceed reversibly. Either a mere enrichment or a separation into multiple target substances can be carried out, in which latter case either the adsorption, the desorption, or both can take place selectively.

Charged ultrafiltration membranes and the method "high-performance tangential flow filtration" (HPTFF) are known in the prior art (for example, from the U.S. Pat. No. 7,153,426 B2). The charge at the membrane surface should improve the retentive filtration selectivity of the ultrafiltration membrane.

The article "Alkaline treatment of the cellulose fiber affecting membrane column behaviour for high-performance immunoaffinity chromatography" by Dongmei Zhou, Hanfa Zou, Hailin Wang, Jianyi Ni, Qiang Zhang, and Yukui Zhang in Biomed. Chromatogr. 14 (2000), 511-515, describes properties of alkaline-solution-treated cellulose fibers which were modified with acrylates and subsequently protein A. The fibers show differences in the accessibilities to proteins, but only slight differences between the alkaline-solution-treated and the untreated fibers.

The present invention uses the following abbreviations:
CA Cellulose Acetate
FPLC Fast Protein Liquid Chromatography
Glob γ-Globulin
GPC Gel-Permeation Chromatography
HPLC High-Pressure Liquid Chromatography
IP Isoelectric Point
Cap Capacity for proteins
kDa kilodalton
KPi Potassium Phosphate buffer
Con Conductivity
Lys Lysozyme
MW Molecular Weight
NaCl Sodium Chloride
NaPi Sodium Phosphate
NaOH Sodium Hydroxide
$Na_2HPO_4$ Disodium Hydrogen Phosphate
S Sulfonic acid
SEC Size-Exclusion Chromatography
UV Ultraviolet An object of the present invention is to provide a method which makes possible a separation of molecules owing to both their different adsorptive properties and their sizes.

These objects are achieved by the subject matter characterized in the claims.

The invention thus provides a method for separating molecules through a combination of membrane chromatography and size-exclusion chromatography.

The separation method according to the invention thus uses the combination of adsorption of adsorbates to the membrane surface and size-exclusion effects. In this way, the selectivity of the adsorptive membrane is improved, leading to possible improvement of working-up processes.

The separation method according to the invention can, for example, be advantageous in specific separation tasks when solely the specificity of the ligand of a membrane adsorber is not sufficient for material separation and the molar masses of the components to be separated are greatly different such that superimposing purely adsorptive material separation with a size-exclusion effect yields altogether an improvement of the separation capacity. A complete separation solely on the basis of this size-exclusion effect is, however, not possible because the size exclusion only becomes effective for the adsorption to the inner surface of the (as defined below) ultrapores, but not to the outer surface of the (as defined below) micropores. The method according to the invention allows, for example, the separation of two identically charged proteins which differ in their size (e.g., lysozyme and γ-globulin) on one cation-exchange membrane.

In the prior art, methods for removing contaminants in so-called negative adsorption are known. Such methods aim for conditions in the media (e.g., pH, conductivity) which make possible the binding of the contaminants to the adsorbent without the target molecule binding to the adsorbent. The purification of monoclonal antibodies often makes use of anion exchangers in the form of membranes or gels for contaminant removal (e.g., DNA, viruses, host cell proteins, leached protein A, aggregates, or endotoxins). With these applications, the pH of the antibody-containing medium should be below the isoelectric point of the antibody, so that the antibody carries the same (positive) charge as the anion exchanger and thus does not bind. However, such a method does not make possible the removal of contaminants which, under the chosen conditions, carry the same charge as the antibody or none at all.

Similarly, cation exchangers can also be used for contaminant removal. It must also be made sure here with cation exchangers known in the prior art that the pH is above the isoelectric point of the antibody. Such a method has various disadvantages: firstly, antibodies can be unstable at higher pHs, leading to possible losses of the product; secondly, contaminants which, under the chosen conditions, carry the same charge as the antibody or none at all do not become depleted.

New methods having improved separation properties are needed for the purification of biopharmaceutical products.

The method according to the invention for material separation is made possible through the pore morphology of a membrane which has a porous double structure consisting of micropores having a diameter in the range from >100 nm to 20 μm, and ultrapores having a diameter of <100 nm and which are not accessible to Blue Dextran having an average molecular weight Mw of 2 000 000, wherein the fraction of the volume of the ultrapores is more than 15% of the entire pore volume accessible to water.

The method according to the invention, using an exchanging membrane of this kind, preferably cation exchanging, makes it possible to choose conditions under which the antibody can bind to the membrane, but occupies only a few binding sites in the micropores of the membrane owing to the antibody size. The antibody amounts which can be bound are below 0.1% of the entire amount and can thus be disregarded. Since the binding sites in the ultrapores of the membrane remain free, smaller, identically charged contaminants can be bound and depleted.

The method according to the invention can also be combined with the known methods, leading to a distinct improvement in contaminant removal. For example, the cation-exchange membranes can be combined with an anion-exchange membrane in one or more apparatuses so that the depletion of a broad spectrum of contaminants is ensured.

In another example, virus purification, it is possible to bind, for example, smaller, charged contaminants, such as DNA fragments, in the ultrapores of an anion-exchange membrane having the mentioned pore morphology of micropores and ultrapores, with the large, identically charged virus molecules flowing through the micropores owing to the size-exclusion limit of the ultrapores and practically not becoming bound in the inner surface of the ultrapores.

The examples shown should illustrate the use of the method according to the invention, but do not imply any limitation of the application possibilities.

A starting material for the adsorption membrane used in the method according to the invention is provided by a cellulose ester membrane which is contacted with at least one solution under conditions which lead firstly to swelling of the cellulose ester matrix and secondly, at the same time, i.e., in situ, to hydrolysis of the ester groups to hydroxyl groups, resulting in a cellulose hydrate membrane.

The swelling of the cellulose ester matrix during the hydrolysis of the ester groups is described by the degree of swelling, i.e., the ratio of the water permeability of the cellulose ester membrane wetted beforehand with water to the water permeability of the final, i.e., hydrolyzed, cellulose hydrate membrane, which has been activatingly crosslinked and optionally provided with ligand(s).

Subsequent to the hydrolysis, the cellulose hydrate matrix obtained is preferably crosslinked by reacting the hydroxyl groups with one or more at least bifunctional reagents, and functional groups (ligands) for enabling adsorptive material separation are then introduced into the crosslinked matrix.

Figure 4:
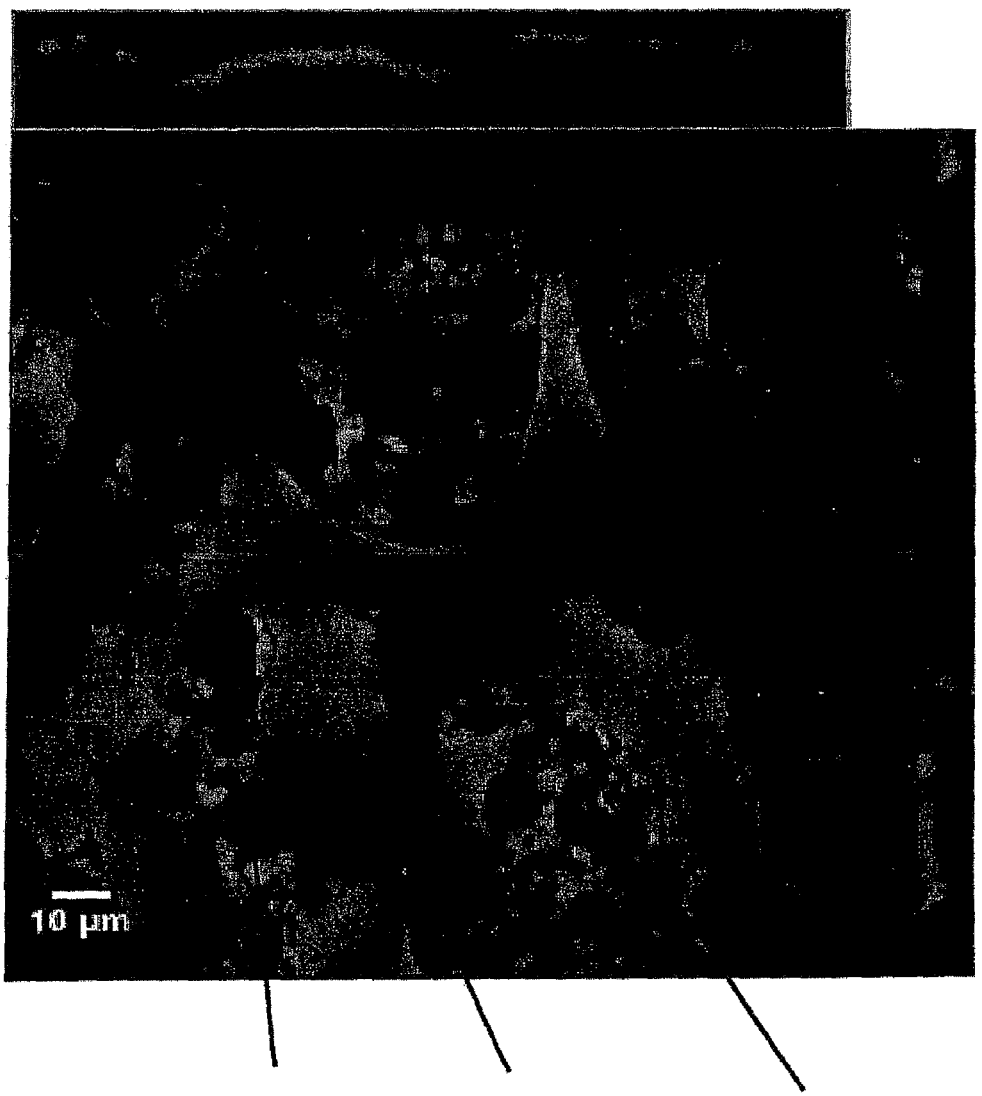

It was found that, surprisingly, the binding capacity of the cellulose hydrate membrane is distinctly increased when the hydrolysis step is carried out under conditions under which the cellulose can swell. The increase in the binding capacity for biomolecules may possibly be caused by the increased number of amorphous regions accessible to biomolecules in the cellulose. Swelling the cellulose support results in two types of pores: a) micropores having a diameter of >100 nm, which are generally smaller than the original pores of the cellulose ester membrane, and b) ultrapores (amorphous regions of the cellulose) having a diameter of <100 nm, which are shaped such that they are not accessible to Blue Dextran (available as Blue Dextran molecular weight 2 000 000 from Sigma, St. Louis, Mo., USA, product number D5751, CAS number: 87915-38-6) and which offer an additional adsorption surface accessible to ligands and adsorbates (cf. FIG. 1c). The effectiveness of adsorption of the membrane according to the invention is not restricted to the phase boundary of the connected micropores with the medium, but extends at least to a portion or even the entire volume in the ultrapores of the support (see FIG. 4). FIG. 4 shows a confocal micrograph of a membrane according to the invention having ultrapores.

The swelling of the cellulose during the hydrolysis can be affected and controlled by a suitable pretreatment of the cellulose ester or by the parameters for hydrolysis (composition of the hydrolysis medium, type of additive, concentration of the additive, hydrolysis temperature). Thus, the permeability and capacity of the membrane can be adjusted. The adsorptive cellulose hydrate membranes produced in the method according to the invention show, compared to the cellulose hydrate membranes produced by production methods known in the field, distinctly higher binding capacities with comparable permeabilities.

As will be described hereinafter, the method for producing the membrane according to the invention can be carried out in three steps, wherein the setting of the desired degree of swelling, of the flow rate, and of the binding capacity can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment of the cellulose ester matrix. High degrees of swelling of the cellulose hydrate matrix can be achieved by the method according to the invention through a high concentration of alkali metal hydroxide in the hydrolysis medium, a high concentration of hydrogen-bond-breaking compounds, or a low temperature of the hydrolysis medium.

Through the type of crosslinking agent, the concentration of the crosslinking agent, the concentration of the crosslinking catalyst, the duration of crosslinking, optionally the type and concentration of an inert organic solvent and/or the crosslinking temperature, it is possible to control the degree of crosslinking, the pore size, and the number of residual active groups, e.g., epoxide groups. As a result, the activation often necessary for the bonding of the functional groups can take place as early as in the crosslinking step.

In a further step, functional groups are bonded, for example, to the hydroxyl groups of the crosslinked membrane. Techniques for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

Preferably, functional groups are bonded to the cellulose membrane via epoxide groups or aldehyde groups. The introduction of the epoxide groups can take place in the crosslinking step or afterwards.

The combinations of the influencing factors (a) of the production conditions of the cellulose ester membrane used as a starting material, (b) of the conditions of any pretreatment carried out, (c) of the hydrolysis conditions, and (d) of the crosslinking conditions of the cellulose ester membrane also make it possible to produce multiple different end products from one starting membrane, resulting in a considerable simplification in terms of production technology.

Starting Membrane

The cellulose ester membrane used as a starting membrane in the method according to the invention has a pore size in the range from 0.1 to 20 µm, preferably from 0.5 to 15 µm, and more preferably from 1 to 10 µm, and is produced by a customary production method known in the field. To determine the pore size, a "capillary flow porometry test" is carried out. Further details can be found in the operating instructions (Capillary Flow Porometer 6.0, CAPWIN Software System, Porous Materials Inc.). Cellulose ester membranes can be composed of cellulose monoacetate, cellulose diacetate, cellulose triacetate, cellulose propionate, cellulose butyrate and cellulose acetobutyrate or other suitable cellulose esters, or cellulose nitrate, methylcellulose or ethylcellulose, and also mixtures thereof, preference being given to cellulose acetates, more particularly cellulose diacetate. It is known to a person skilled in the art that the cellulose ester membrane can, in part, also contain hydroxyl groups in addition to the ester groups.

Pretreatment

Before the hydrolysis, the cellulose ester membrane can be pretreated in a suitable medium. The temperature in the pretreatment step is preferably in a range from 20 to 100° C., particular preference being given to a temperature in a range from about 60° C. to about 80° C. A gas, such as, for example, air, an organic solvent, such as, for example, an alcohol, or an aqueous medium can be used as a pretreatment medium, preference being given to an aqueous medium. The pretreatment medium comprises preferably one or more additives which have a dissolving or plasticizing effect on a cellulose ester. Suitable additives are, in particular, acids, more particularly carboxylic acids, such as acetic acid, and water-soluble plasticizers for cellulose esters, such as diacetin, triacetin, and sulfolane. However, it is particularly preferred, in particular for commercial reasons, to use acetic acid as an additive for the pretreatment medium; although diacetin and triacetin also deliver excellent results, they are more expensive. The concentration of the additive in the pretreatment medium is not subject to any particular restrictions.

The duration of the pretreatment has no substantial influence on the pretreatment effect, provided that a minimum exposure time is applied which ensures a temperature equalization of the cellulose ester membrane in the pretreatment medium and a concentration equalization of any additive used in the membrane. The upper limit of the exposure time of the pretreatment medium is determined by the time from which a chemical reaction of the cellulose ester membrane with the pretreatment medium, for example by hydrolysis, could occur. In other words, the exposure time of the pretreatment medium is set such that no (premature) hydrolysis of the pretreated cellulose ester membrane occurs. Usually, the exposure time of the pretreatment medium to the cellulose ester starting membrane is between 0.1 second and 1 hour, preference being given to an exposure time in the range from 10 seconds to 10 minutes. The extent of the pretreatment effect is dependent on the highest temperature in conjunction with the highest concentration of the additive which affect the cellulose ester membrane. Thus, when the cooling or rinsing-out of the additive takes place over a longer period, this has no influence on the pretreatment effect already achieved. The pretreatment can therefore be terminated by rinsing the pretreatment additive out of the membrane and/or lowering the temperature of the pretreatment medium.

Hydrolysis

The optionally pretreated cellulose ester membrane is hydrolyzed with a suitable hydrolysis medium, whereby the cellulose hydrate membrane forms by swelling of the cellulose matrix. Depending on the type of pretreatment medium, the cellulose ester membrane can be used dry or wet in the hydrolysis step.

Through the swelling of the cellulose, the accessibility of the hydroxyl groups for the attachment of the functional groups and subsequently for the adsorbates is improved. The hydrolysis of the cellulose ester membrane is preferably carried out in an aqueous medium. More preferably, an aqueous hydrolysis medium having a pH of >7, i.e., a basic medium, is used. The hydrolysis medium comprises preferably an alkaline compound, preferably an alkali metal hydroxide. It is particularly preferred to use an aqueous solution of sodium hydroxide or lithium hydroxide. Use can also be made of mixtures of one alkali metal hydroxide and other alkaline compounds, such as alkali metal carbonate, such as sodium carbonate, potassium carbonate, cesium carbonate, sodium hydrogen carbonate, and/or sodium triphosphate, potassium triphosphate, sodium silicate and potassium silicate.

The concentration of the alkaline compound in the hydrolysis medium can be up to about 50% by weight, preference being given to a concentration in the range from 0.1 to 50% by weight and particular preference to a concentration in the range from 0.4 to 10% by weight. In a particularly preferred embodiment of the present invention, a hydrolysis medium composed of water and sodium hydroxide is used, the concentration of the sodium hydroxide in the hydrolysis medium being preferably in a range from 0.1 to 20% by weight, particularly preferably in a range from 0.4 to 4% by weight.

The hydrolysis medium can comprise one or more additives which have a swelling-influencing effect on a cellulose ester. Suitable additives are, in particular, salts, such as sodium chloride, sodium sulfate, and sodium acetate, hydrogen-bond-breaking compounds, such as urea, or organic solvents, such as ethylamine. The organic solvent is preferably selected from the group consisting of alcohols, ketones, and ethers. Particularly preferred solvents are ethanol, methanol, ethylene glycol, propylene glycol, glycerol, acetone, dioxane, or diglyme. The additive in the hydrolysis medium should influence the swelling, but not completely suppress it.

The temperature of the medium used in the hydrolysis step can be in the range from about 10° C. up to the boiling point of the hydrolysis medium, preference being given to a temperature in a range from 15° C. to about 25° C.

The duration of hydrolysis is determined by the composition of the hydrolysis medium and the hydrolysis temperature. Usually, the duration of hydrolysis is in the range from 0.1 to 60 minutes, preference being given to a duration of hydrolysis in the range from 5 to 45 minutes. A particularly preferred duration of hydrolysis in the range from 20 to 40 minutes.

Crosslinking

The cellulose hydrate membrane obtained following any pretreatment carried out and following the hydrolysis with swelling is crosslinked with a crosslinking agent to increase the chemical resistance of the membrane and/or to introduce functional groups.

The crosslinking agent has at least two functional groups in the molecule which are reactive with the hydroxyl groups of cellulose and thus make crosslinking of cellulose possible. The usable crosslinking agents are, in principle, not subject to any particular restrictions and a person skilled in the art is capable of selecting them from a series of crosslinking agents usable for the crosslinking of cellulose. However, it is preferred to use, in the crosslinking step, a diepoxide compound or else other compounds which are reactive with hydroxyl groups of cellulose and have at least two reactive functional groups, such as diisocyanate, epichlorohydrin, epibromohydrin, dimethylurea, dimethylethyleneurea, dimethylchlorosilane, bis(2-hydroxyethyl)sulfone, divinyl sulfone, alkylene dihalogen, hydroxyalkylene dihalogen, and glycidyl ethers.

From the group of the glycidyl ethers, preference is given to 1,4-butanediol diglycidyl ether, ethylene glycol diglycidyl ether, glycerol diglycidyl ether, and polyethylene glycol diglycidyl ether.

Particular preference is given to the use of 1,4-butanediol diglycidyl ether or epichlorohydrin as a crosslinking agent.

Optionally, a mixture of different crosslinking agents can be used.

The crosslinking can take place in an aqueous medium, in an organic solvent, or else in a mixture of water and an organic solvent. Preferably, the crosslinking is carried out in an aqueous medium.

It is further preferred to use a crosslinking catalyst, such as sodium hydroxide, to accelerate the crosslinking of cellulose with the crosslinking agent.

The temperature of the medium used in the crosslinking step can be in the range from about 4° C. up to the boiling point of the crosslinking medium, preference being given to a temperature in a range from 5° C. to about 70° C. A particularly preferred temperature is in the range from 20° C. to 40° C.

Usually, the duration of crosslinking is in the range from 10 minutes to 100 hours, preference being given to a duration of crosslinking in the range from 30 minutes to 48 hours. A particularly preferred duration of crosslinking is in the range from 2 to 24 hours.

As described above, the method for producing the membrane according to the invention can be carried out in three steps, wherein the setting of the desired degree of swelling of the matrix can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment.

Activation and Bonding of Ligands

In a further step, sulfonic acid ligands are bonded to the hydroxyl groups of the crosslinked cellulose hydrate membrane. Techniques for bonding functional groups, such as, for example, sulfonic acid ligands, are known to a person skilled in the art (e.g., from Greg T. Hermanson, A. Krishna Mallia, Paul K. Smith, Immobilized Affinity Ligand Techniques, Academic Press, INC, 1992).

Preferably, the ionic and/or hydrophobic ligands are bonded to the cellulose membrane via epoxide groups or aldehyde groups. The epoxide activation can take place as early as in the crosslinking step or afterwards.

It is also possible to introduce the ligands during the crosslinking, e.g., by adding an amine and/or a monofunctional epoxide compound, such as phenyl glycidyl ether or butyl glycidyl ether, to the diepoxide compound.

The membranes according to the invention can, after the introduction of the ligands, optionally be dried. Membranes can be directly dried to remove water or organic solvents, preferably alcohol, or can be dried after carrying out a step-wise replacement of water with an organic solvent. Preferably, the membranes are dried to remove a medium which comprises a pore-stabilizing compound. Particularly preferably, the membranes according to the invention are dried to remove an aqueous glycerol solution. The concentration of the glycerol is preferably in the range from 5 to 40% by weight, based on the aqueous solution.

Explanation of the Examples

Crosslinked cellulose hydrate membranes having a low degree of swelling are, for example, produced from cellulose ester membranes hydrolyzed with ethanolic potassium hydroxide solution. A cellulose acetate membrane yields, in this way, a crosslinked cellulose hydrate membrane which has a negligibly low flow rate (see example 1), but which has, after introduction of ligands, virtually no adsorption capacity (see table 3).

It has now been found that, although hydrolysis with an aqueous sodium hydroxide solution lowers the flow rate (see example 2), distinctly increased binding capacities occur following overlaying with various ligands, increasing sodium hydroxide solution concentrations resulting in a stronger flow rate reduction and higher binding capacities (see table 3). Compared with the membrane-penetrating micropores which mainly form in the hydrolysis with ethanolic potassium hydroxide solution, the formation of a multiplicity of small ultrapores appears to be preferred in the hydrolysis with aqueous sodium hydroxide solution. A higher hydrolysis temperature and also an additional content of electrolytes, including sodium acetate already formed in the hydrolysis, have the same effect as a lower sodium hydroxide solution concentration.

WO 2007/017085 A2 describes a method for producing crosslinked cellulose hydrate membranes which consists in the simultaneous hydrolysis and crosslinking of cellulose ester membranes and is intended to be equally suitable for filtration and adsorption membranes. One of the goals of the invention described therein is the hydrolysis and crosslinking of the cellulose ester under conditions which do not affect the structure and permeability of the membrane. Through simultaneous hydrolysis and crosslinking under conditions which suppress swelling and structural change ($Na_2SO_4$, low sodium hydroxide solution concentration), no significant binding capacity is found (see comparative example 2). Only when the alkaline solution concentration is increased is there an increase in the binding capacity. However, the swelling of the cellulose here also leads to a change in the pore structure, contrary to the simultaneous hydrolysis and crosslinking process described in the prior art. The binding capacity here is, however, only about 5% of the binding capacity in comparison with the hydrolysis and crosslinking carried out separately (see example 2 and comparative example 2).

Furthermore, it has been found that different pretreatment of the cellulose acetate membrane has different effects on the properties of the adsorptive membrane according to the invention. The flow rate decreases and the binding capacity increases when the cellulose acetate membrane has been heated to 80° C. under air prior to the hydrolysis (see example 3). When the cellulose acetate membrane is heated to 80° C. in 20% acetic acid prior to the hydrolysis (see example 4), the flow rate increases in comparison with the non-pretreated membrane from example 2 and the binding capacity changes depending on the size of the protein. The binding capacity increases for lysozyme (MW: 14.3 kDa); the binding capacity decreases for bovine serum albumin (BSA; MW: 60 kDa) and γ-globulin (MW: 150 kDa). The ultrapores in the cellulose matrix become smaller, and the selectivity of the membrane becomes higher. Selectivity here is defined as the ratio of the binding capacity (Cap) for one protein, for example, lysozyme (Lys), to the binding capacity (Cap) for another protein, for example, γ-globulin (Glob), expressed in mg/cm² of membrane area, i.e., for example the quotient CapLys/CapGlob.

The higher the selectivity, the greater the contribution made by the size-exclusion effect alongside the adsorption. The selectivity can also be influenced by the binding conditions, such as, for example, the pH or the salt concentration. Thus, the selectivity in a 10 mM potassium phosphate (KPi) buffer having a pH of 7.0 is higher than the selectivity in a 20 mM sodium acetate+50 mM NaCl buffer having a pH of 5.0. Compared with a membrane known in the prior art, for example, a Sartobind® S membrane from Sartorius Stedim Biotech GmbH, the selectivity of a membrane according to the invention (cf. example 4) is up to about 8 times higher.

The following overview reports the binding capacities and selectivities of the membranes according to the invention of examples 2 and 4 in comparison with a standard membrane (Sartobind® S membrane) with regard to the proteins lysozyme and γ-globulin under various operating conditions.

| Membrane | Protein | Binding buffer | Binding capacity [mg/cm²] | Selectivity[3] |
|---|---|---|---|---|
| Example 2 | Lysozyme | A[1] | 2.82 | 14.8 |
| | γ-Globulin | A | 0.19 | |
| | Lysozyme | B[2] | 1.93 | 4.4 |
| | γ-Globulin | B | 0.44 | |
| Example 4 | Lysozyme | A | 3.17 | 24.4 |
| | γ-Globulin | A | 0.13 | |
| | Lysozyme | B | 2.23 | 9.7 |
| | γ-Globulin | B | 0.23 | |
| Sartobind ® S | Lysozyme | A | 1.13 | 3.1 |
| | γ-Globulin | A | 0.36 | |
| | Lysozyme | B | 1.00 | 1.3 |
| | γ-Globulin | B | 0.75 | |

[1] Binding buffer A: 10 mM KPi buffer having pH 7.0
[2] Binding buffer B: 20 mM sodium acetate + 50 mM NaCl having pH 5.0
[3] Selectivity is defined as the ratio of the binding capacity for lysozyme to the binding capacity for γ-globulin, expressed in mg/cm² of membrane area The pretreatment can, for example, be advantageous in specific separation tasks when solely the specificity of the ligand is not sufficient for material separation, and the molar masses of the components to be separated are so different that the overall result of superimposing a size-exclusion effect on purely adsorptive material separation is an improvement in the separation capacity, and the influencing of the pore size of the ultrapores through choice of base and its concentration needs support. A complete separation solely on the basis of this effect is, however, not possible because the size exclusion only becomes effective for the adsorption on the inner surface of the ultrapores, but not on the outer surface of the micropores.

These findings indicate, in the case of hydrolysis and crosslinking of cellulose acetates, complex swelling and deswelling procedures whose effects with regard to the structure of the end product are difficult to summarize because there are both procedures in which a flow rate reduction is coupled with an increase in the binding capacity and procedures in which this is not the case. The former are referred to hereinafter as "productive", the others as "unproductive". The pretreatment of the cellulose acetate membrane has different effects on the change in pore structure, and the formation of micropores and also of ultrapores. It is thus possible, through a suitable choice of the pretreatment, to influence the flow rate, the binding capacity but also the size exclusion of the adsorptive membrane according to the invention. The main goal of the method according to the invention is the restriction to productive flow rate reductions, which should take account not only of the swelling behavior of the starting material, the cellulose acetate membrane, and the end product, the crosslinked cellulose hydrate membrane, but also the entire spectrum of the intermediate products in the partially hydrolyzed and partially crosslinked state. For example, it is known that cellulose acetates of decreasing acetyl content even pass through, in a narrow range, a state of water solubility.

According to the invention, a cellulose ester membrane is sequentially hydrolyzed in a swelling medium, preferably an aqueous solution of an alkali metal hydroxide, crosslinked with an at least bifunctional agent, and provided with an adsorption-effective ligand. The swelling capacity of the alkali metal hydroxides increases with smaller cation radii and higher concentrations (see example 5).

The cellulose is preferably crosslinked according to the invention with 1,4-butanediol diglycidyl ether. In an embodiment of the invention, the cellulose is crosslinked with 1,4-butanediol diglycidyl ether such that, because of a partly one-sided reaction, a sufficient number of unreacted epoxide groups are preserved ("activating crosslinking", see example 2) and can serve to bond or to couple or to construct ligands. The unreacted epoxide groups are relatively hydrolysis-stable and were used for subsequent reactions even after humid storage at room temperature for up to 24 hours. In another embodiment of the invention for bonding "active" ligands, the crosslinking is carried out under more severe conditions (longer duration of crosslinking and/or higher alkali concentration and/or higher temperature) so that, with increased reaction with the cellulose and/or increased hydrolysis of the surplus groups, virtually no epoxide groups remain ("nonactivating crosslinking", see example 6). Remaining epoxide groups can also be hydrolyzed by subsequent treatment with, for example, 5% sulfuric acid at an elevated temperature.

The flow rate of the membrane according to the invention in example 2 for a 20 mM Tris/HCl buffer having a pH of 7.3 is 8% greater than that for pure water. Corresponding values for adsorption membranes which were produced by coating according to the prior art are in the range from 20%, in the case of a crosslinked auxiliary polymer, to 200%, in the case of an uncrosslinked auxiliary polymer. The resulting pore structure, by virtue of the low dependence of the flow rate on the ionic strength of the medium, appears to be a hybrid of aerogel and xerogel, similar to a crosslinked agarose gel. This is consistent with the fact that the introduction of hydrophobic ligands also leads to a capable adsorption membrane for hydrophobic interaction chromatography (HIC) (see examples 4 and 10).

It is difficult to distinguish the adsorption membranes according to the invention from adsorption membranes produced by polymer coating or grafting according to the prior art by scanning electron microscopy because its resolution would be overwhelmed by the small-pored structures (i.e., ultrapores) which constitute the main difference. In contrast, the characterization of adsorptive membranes by means of confocal laser scanning microscopy (CLSM) simultaneously delivers, under suitable conditions, information both about the pore structure and about the distribution of protein bound to functional groups in the membrane. For this purpose, the membrane material and protein have to be labeled with two different fluorescent dyes. All microscopic measurements were carried out at approximately the same distance (about 20 μm) from the respective outer surface. In all cases, three independent measurements at different x,y-positions led to very similar results characteristic of the respective membrane type.

Characteristic of all membrane samples is a very coarse structure (dark areas in FIGS. 2-4) composed of relatively thick fibers or their agglomerates interspersed with more finely distributed fibroid or clusterlike membrane material with completely or partially undyed areas which can be attributed to the membrane-penetrating micropores having dimensions of up to about 20 μm. The protein distribution was clearly identifiable for all membrane samples. However, very great differences with regard to protein amount (fluorescence intensity, bright areas) and protein distribution in the pore structure (dark areas) were found. The total fluorescence intensities were distinctly different; for the membrane according to the invention in example 2, it was even necessary to select a lower amplification than for the other membranes: Membrane from example 2>Sartobind® S membrane>>Membrane from example 1

These results correlate well with the figures for the binding capacity:
Membrane according to example 1: 0.01 mg/cm$^2$
Sartobind® S membrane: 0.90 mg/cm$^2$
Membrane according to example 2: 2.06 mg/cm$^2$ Using the investigative technique, it was possible to identify clear and great differences with regard to protein binding between the established Sartobind® S membrane (FIG. 2) and the membranes functionalized with sulfonic acid ligands from example 1 (FIG. 3) and example 2 (FIG. 4). With the membranes from examples 1 and 2, the fluorescence intensities for the protein (bright areas) correlate with the nominal protein-binding capacities, i.e., the membrane from example 1 exhibits only a very low binding capacity, while the membrane according to the invention from example 2 exhibits a distinctly higher binding capacity.

The protein in the Sartobind® S membranes, based on the same pore structure of the base support, binds, in particular, in the volume of the micropores, a three-dimensional functional layer being essential for the protein binding. These membranes show, at the edges of the pores, sharp boundaries between the material of the membrane (dark areas) and the protein layer (bright areas). Because of the restricted range of this functional layer, small fractions of the pore volume remain in which no protein is bound. In the case of the membrane from example 1, the binding takes place directly on the membrane material, recognizable by small, bright points in FIG. 2. In contrast to this, in the case of the membrane according to the invention from example 2, clearly very large amounts of protein are bound in the ultrapores of the coarse fiber structure and also in the more finely distributed fibroid or clusterlike membrane material. Between the distributions of cellulose and protein, a very good correlation is found, also recognizable visually from the fact that only the mixed color of the dyes used is recognizable in the overlay, because both pore surface and protein are visible in the depth of the ultrapores. By far the largest fraction of the volume of the micropores contains no protein.

In order to quantify the ultrapores of the membranes according to the invention, an experiment was carried out in which the accessibility of the pores to Blue Dextran was determined. The experiment was carried out in the manner described in example 14. The result of the evaluation is shown in table 1 and in FIG. 5.

Figure 5:
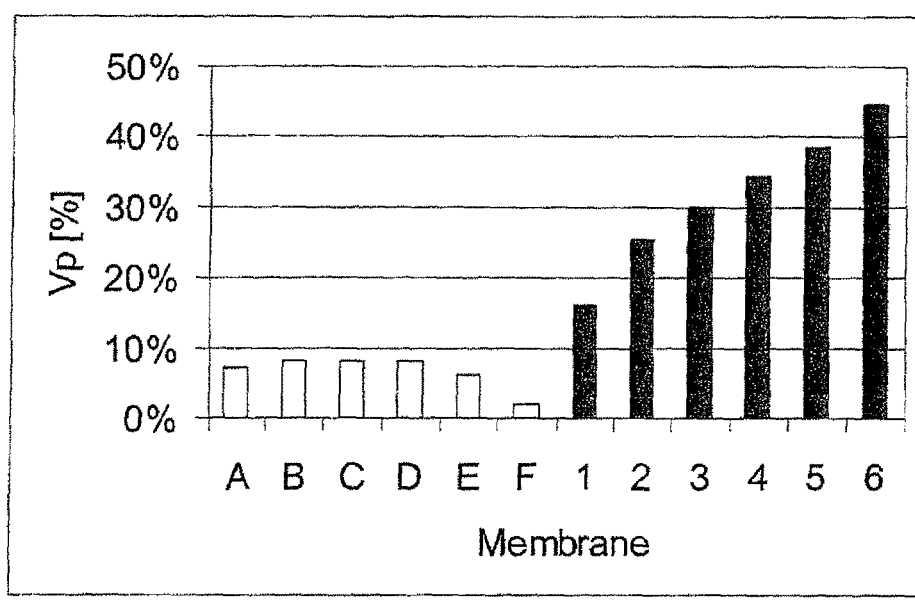

In FIG. 5, a distinct difference is recognizable between the ultrapores inaccessible to Blue Dextran for the membranes A-F known in the prior art and membranes according to the invention from example 14. In the case of the membranes according to the invention, which were hydrolyzed under swelling conditions, more than 15% of the entire pore volume is in the range of ultrapores (i.e., pores having a diameter <100 nm which are not accessible to Blue Dextran), whereas it is less than 8% for the comparative membranes A-F.

Accordingly, membranes according to the invention have a volume of ultrapores which are accessible to water, but not to Blue Dextran having a molecular weight Mw of 2 000 000, of more than 15%, preferably more than 18%, more preferably more than 20%, even more preferably more than 25%, and most preferably more than 30% of the entire pore volume.

FIGURES

FIG. 1a): Schematic illustration of the binding of protein to micropores of an adsorptive membrane known in the prior art and produced as in example 1.

FIG. 1b): Schematic illustration of the binding of protein to an adsorptively active polymer coating of adsorptive membranes as described in the prior art which consist of one or more support structures and one or more adsorptively active polymer coatings.

FIG. 1c): Schematic illustration of the binding of protein in the ultrapores of an adsorptive membrane according to the invention.

Figure 2:
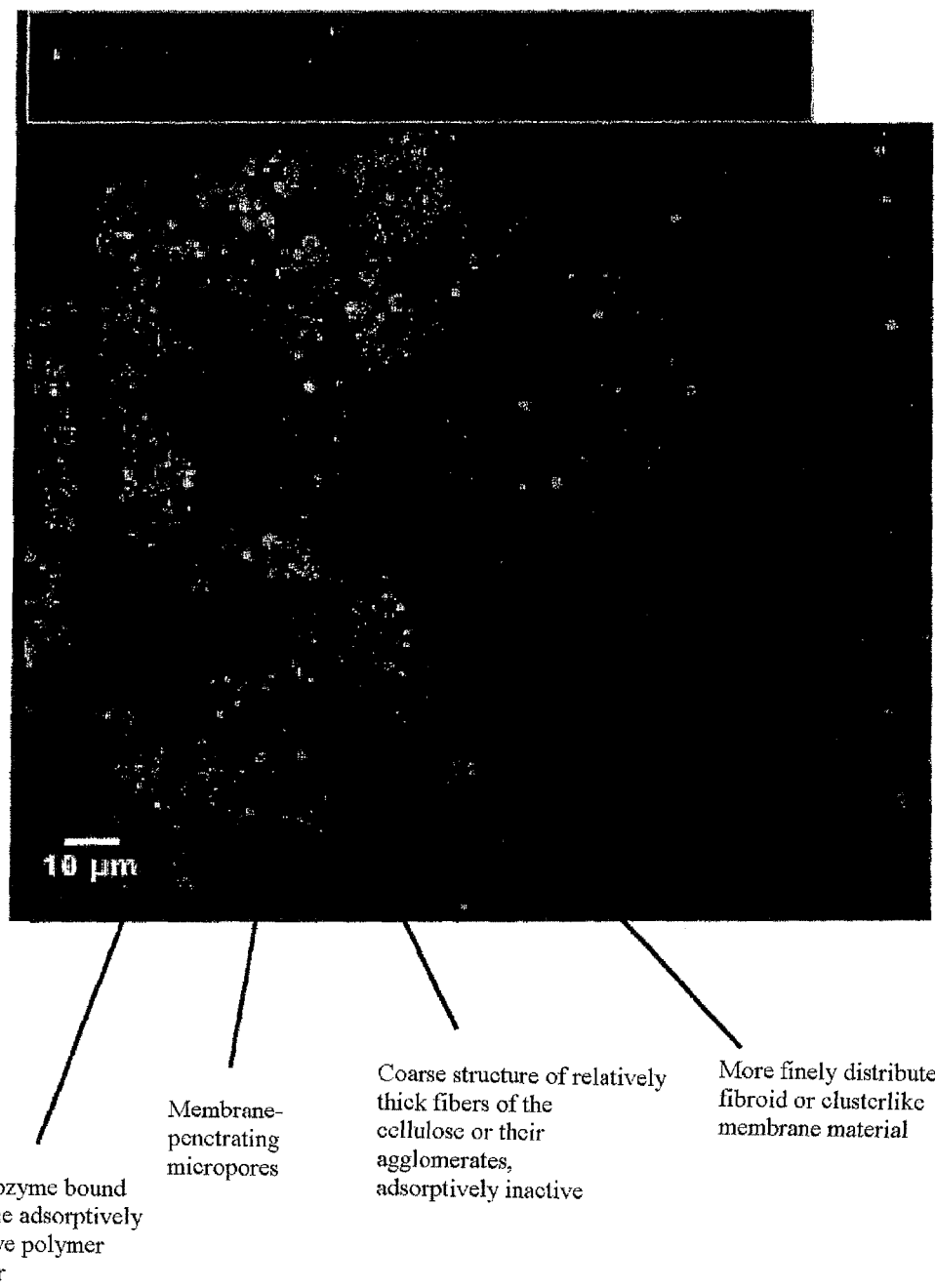

FIG. 2: CLSM image of the pore morphology and protein distribution on the upper side of the Sartobind® S membrane following labeling of the cellulose with fluorescent dye and loading with fluorescently labeled lysozyme.

Figure 3:
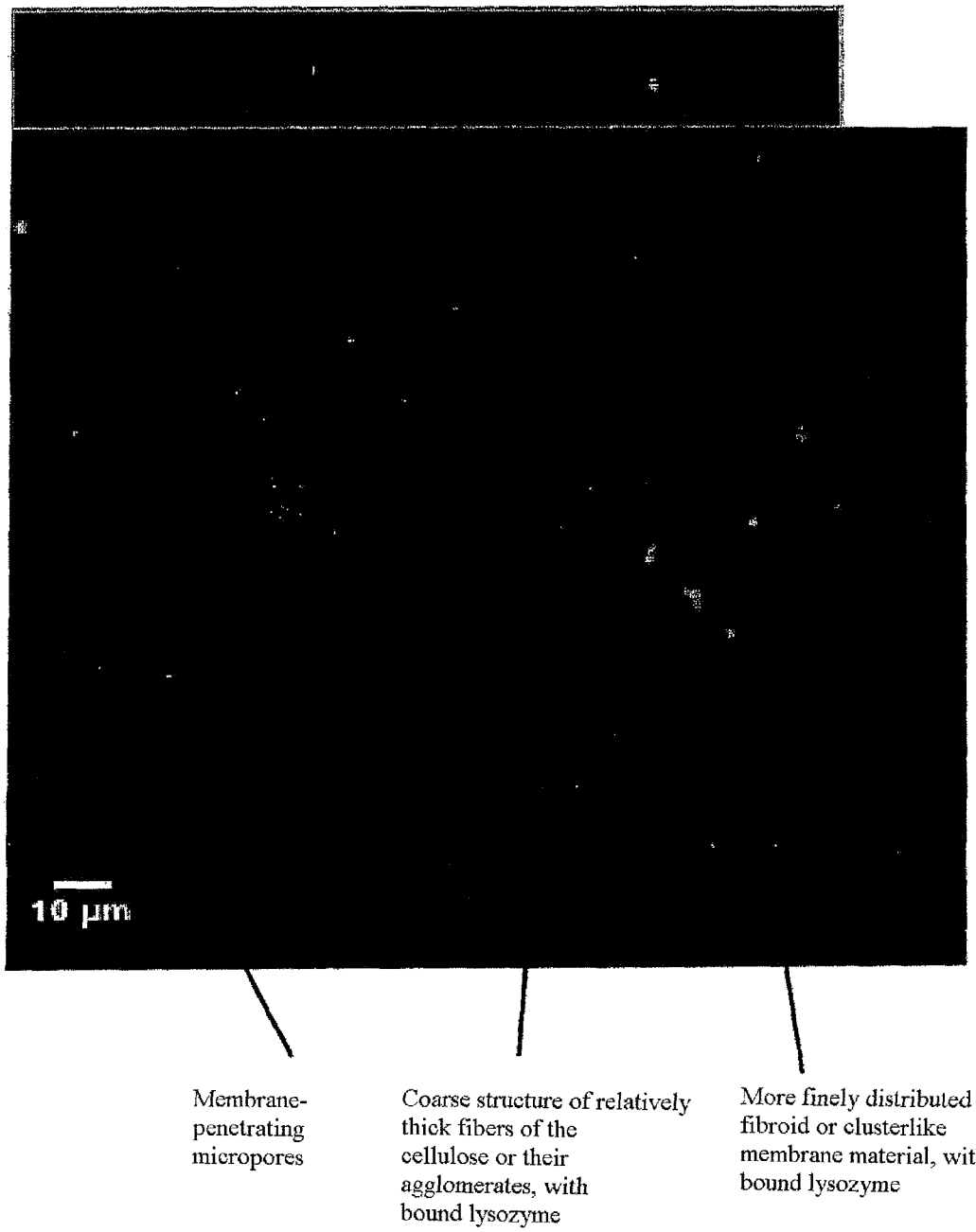

FIG. 3: CLSM image of the pore morphology and protein distribution on the upper side of the membrane reacted with sulfonic acid ligands according to example 1 following labeling of the cellulose with fluorescent dye and loading with fluorescently labeled lysozyme.

FIG. 4: CLSM image of the pore morphology and protein distribution on the upper side of the membrane reacted with sulfonic acid ligands according to example 2 following labeling of the cellulose with fluorescent dye and loading with fluorescently labeled lysozyme.

FIG. 5: Comparison of the percentage of pores inaccessible to Blue Dextran having a molecular weight Mw of 2 000 000 in the membranes:
A: Membrane from example 1
B-F: Cellulose membranes according to the prior art, 0.2-0.45 μm, from Sartorius Stedim Biotech GmbH
1-6: Membranes according to the invention from example 14

Figure 6:
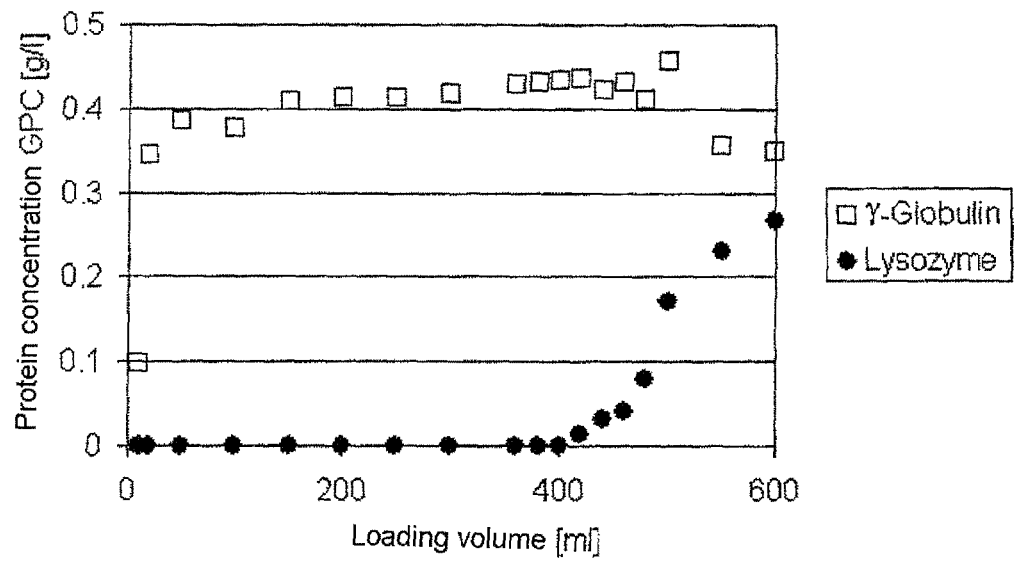

FIG. 6: Breakthrough curve for lysozyme and γ-globulin from example 15, plotted from the GPC analyses of the individual fractions.

Figure 7:
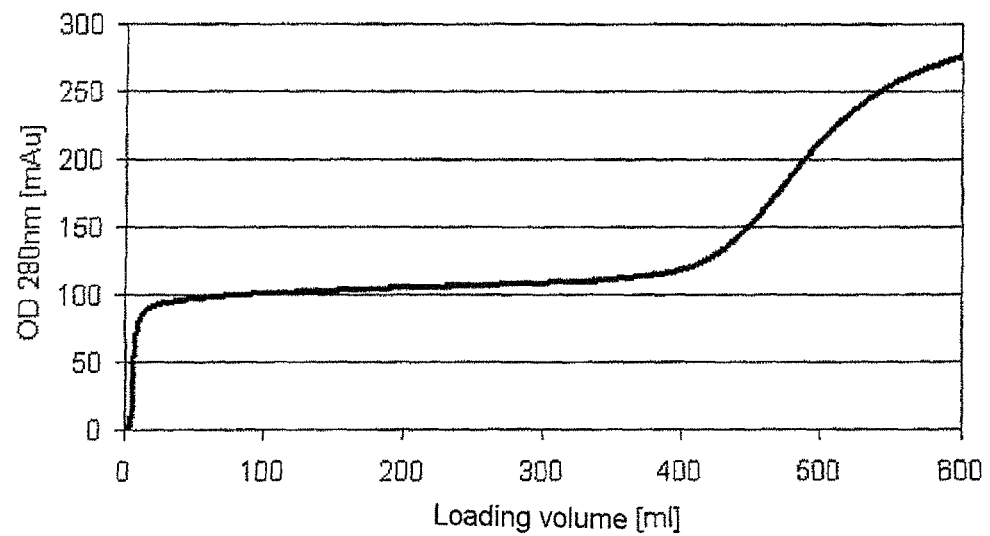

FIG. 7: Breakthrough curve for lysozyme and γ-globulin from example 15, plotted as a result of detection of the absorbance (optical density OD) at 280 nm.

Figure 8:
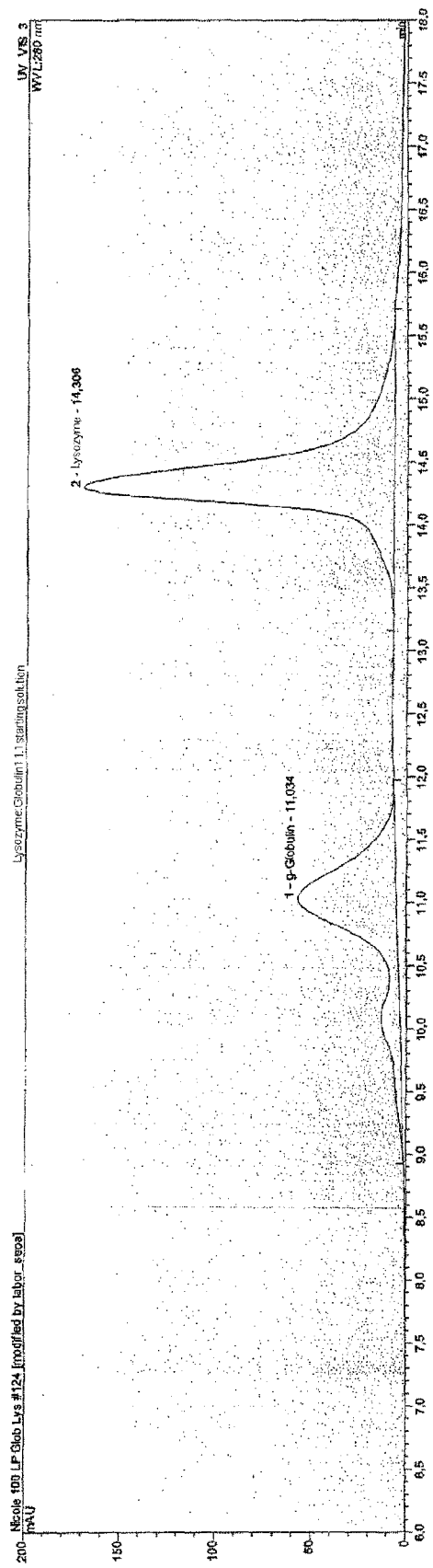

FIG. 8: GPC analysis of the starting solution from example 15.

Figure 9:
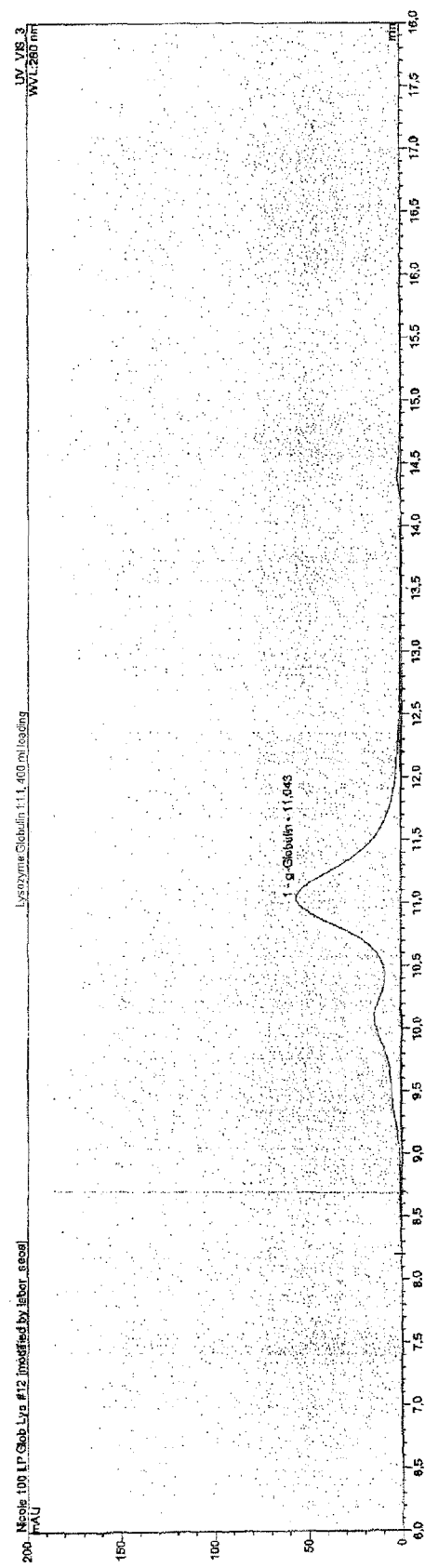

FIG. 9: GPC analysis of the fraction of the flow-through after a 400 ml loading of the membrane from example 15.

Figure 10:
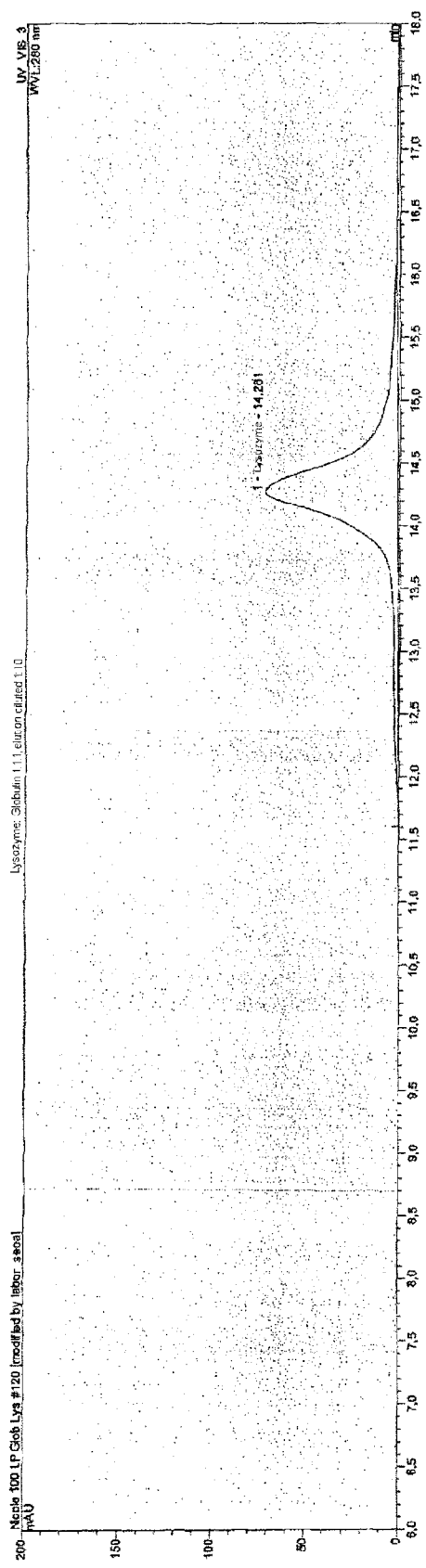

FIG. 10: GPC analysis of the elution fraction (diluted 1:10) from example 15.

Figure 11:
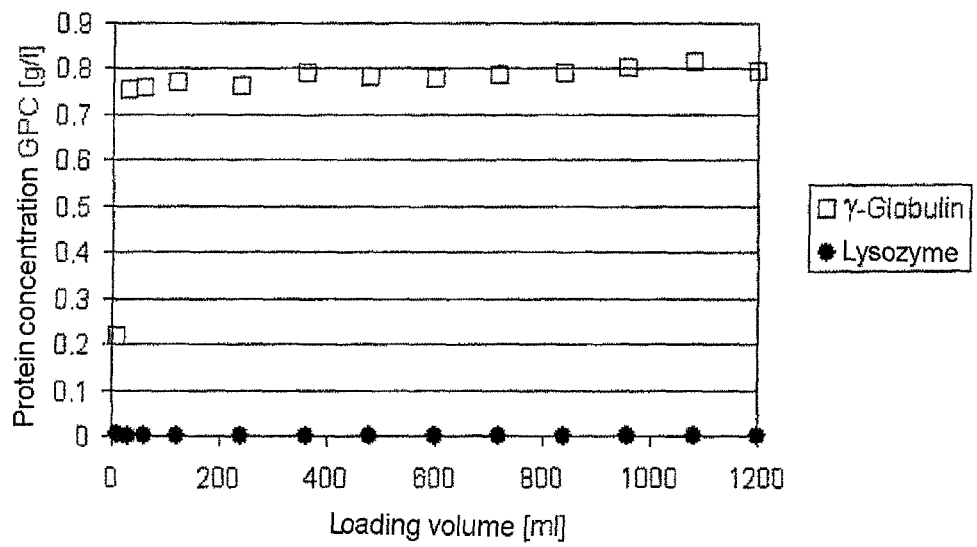

FIG. 11: Breakthrough curve for lysozyme and γ-globulin from example 16, plotted from the GPC analyses of the individual fractions.

Figure 12:
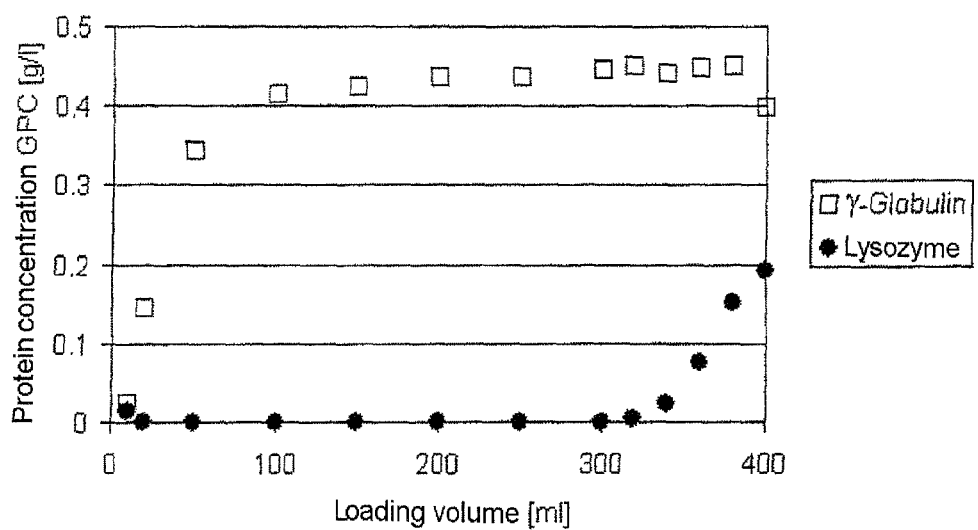

FIG. 12: Breakthrough curve for lysozyme and γ-globulin from example 17, plotted from the GPC analyses of the individual fractions.

Figure 13:
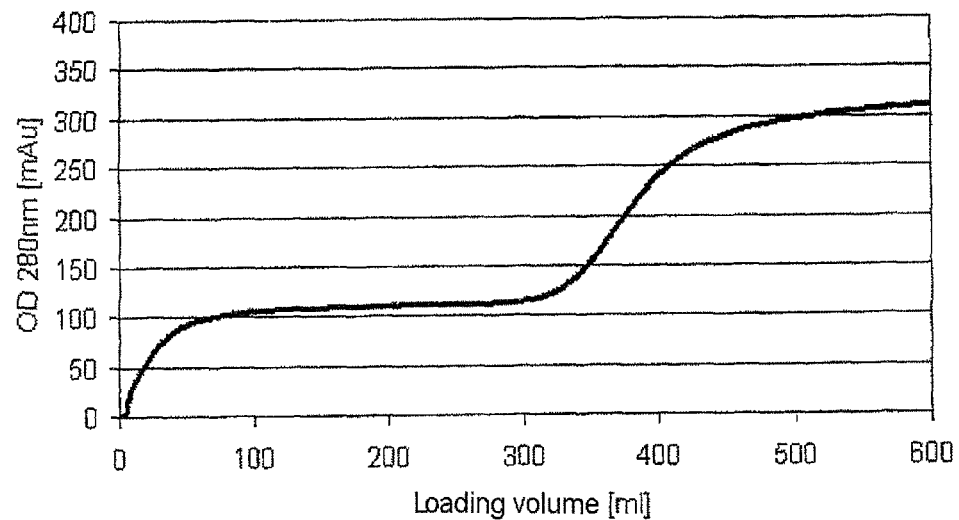

FIG. 13: Breakthrough curve for lysozyme and γ-globulin from example 17, plotted as a result of detection of the absorbance (optical density OD) at 280 nm.

Figure 14:
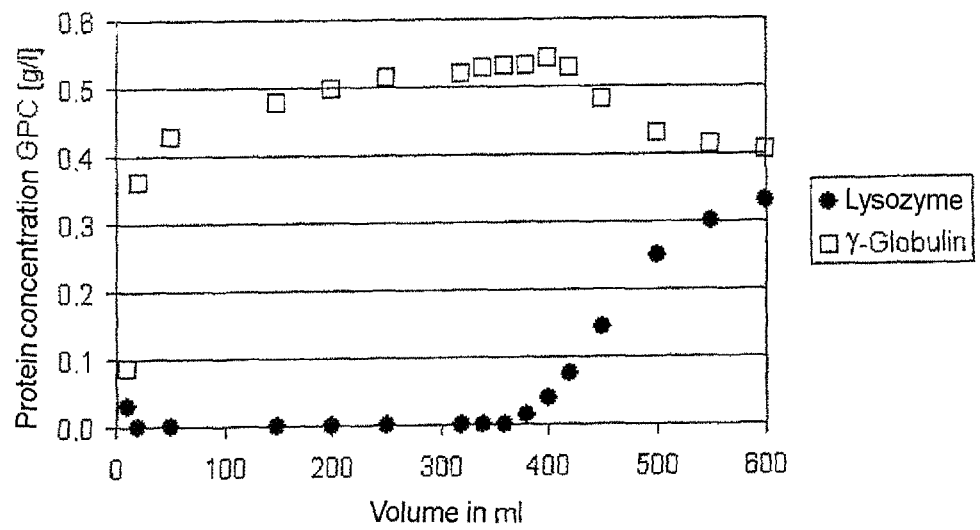

FIG. 14: Breakthrough curve for lysozyme and γ-globulin from example 18, plotted from the GPC analyses of the individual fractions.

Figure 15:
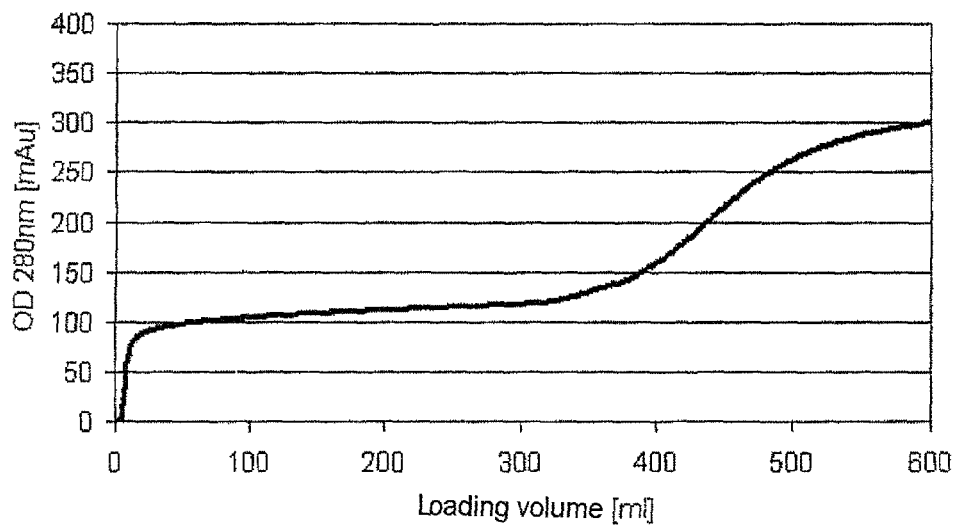

FIG. 15: Breakthrough curve for lysozyme and γ-globulin from example 18, plotted as a result of detection of the absorbance (optical density OD) at 280 nm.

Figure 16:
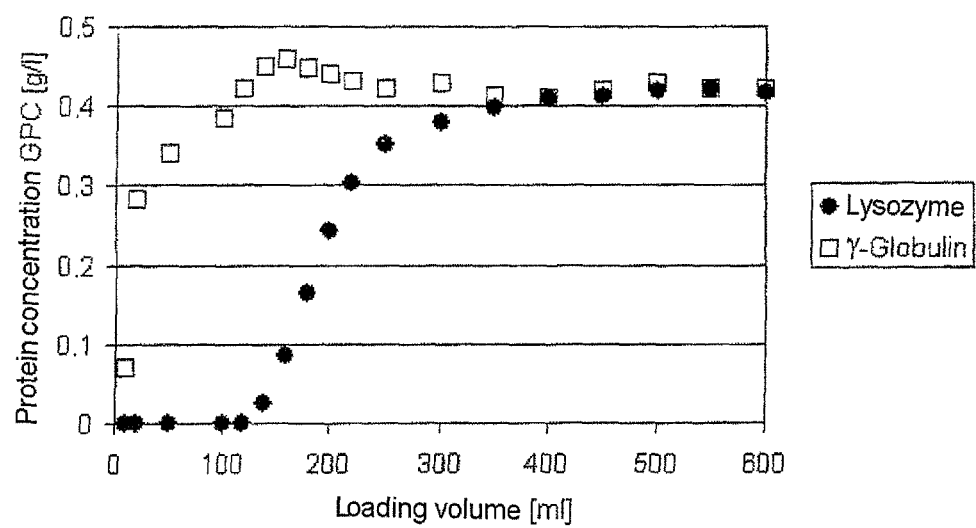

FIG. 16: Breakthrough curve for lysozyme and γ-globulin from comparative example 1, plotted from the GPC analyses of the individual fractions.

Figure 17:
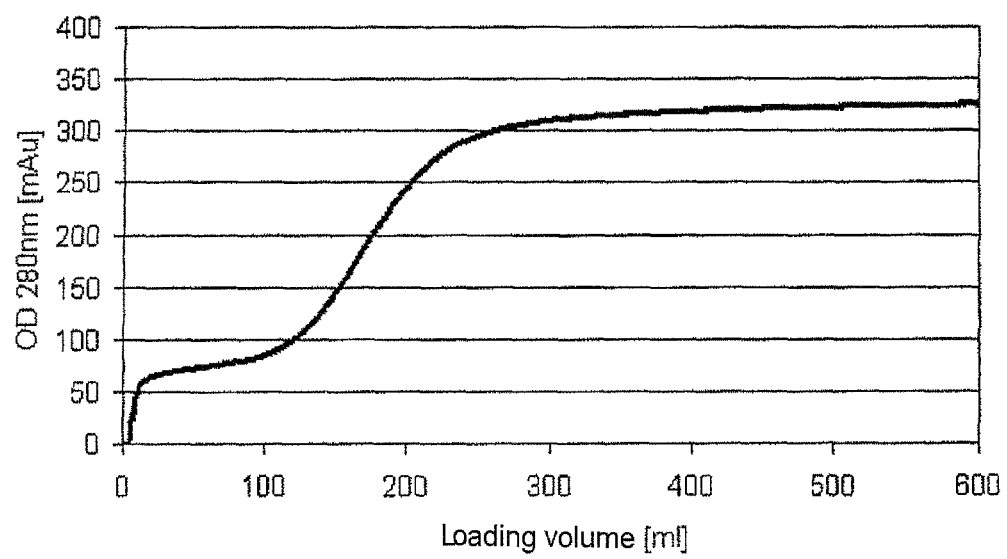

FIG. 17: Breakthrough curve for lysozyme and γ-globulin from comparative example 1, plotted as a result of detection of the absorbance (optical density OD) at 280 nm.

EXAMPLES

All mention in the examples of a CA membrane refers to a polyester-nonwoven-reinforced type of cellulose acetate membrane having a pore diameter of about 3 μm (measured with a Coulter Capillary Flow Porometer 6.0, CAPWIN Software System, Porous Materials Inc.) and having a water flow rate of 730 ml/(min×bar×cm$^2$). The thickness of the modified membrane samples was, on average, 250 μm. All flow rate figures are in ml/(min×bar×cm$^2$), and all binding capacity figures are in mg/cm$^2$. Unless stated otherwise, percentages are based on weight.

Example 1

Activatingly Crosslinked Cellulose Hydrate Membrane Having a Low Degree of Swelling for Comparative Examples The membrane was produced in the following way: A CA membrane, as mentioned above, was used as starting material. This CA membrane was hydrolyzed for three minutes at room temperature with a 15% potassium hydroxide solution in 80% ethanol. Subsequently, it was rinsed for three minutes with a 6.8% acetic acid solution, twice with ethanol, and then for 15 minutes with running reverse-osmosis (RO) water. Afterwards, the membrane was dried for 20 minutes at 80° C. in a circulating air drying cabinet.

In the next step, the dried membrane thus obtained was treated for 30 minutes at room temperature with 30% 1,4-butanediol diglycidyl ether in an aqueous 0.1 M sodium hydroxide solution and aqueous 0.1% sodium borohydride solution, and then the moist membrane was left to stand for 20 hours in a closed vessel at room temperature.

Finally, the membrane was rinsed for 30 minutes with running water.

The water flow rate of the activatingly crosslinked cellulose hydrate membrane thus produced was 630 ml/(min×bar×cm$^2$). The degree of swelling was 1.16.

Example 2

Activatingly Crosslinked Intermediate Product for an Adsorption Membrane According to the Invention A CA membrane, as in example 1, was used as starting material. This CA membrane was hydrolyzed for 30 minutes at room temperature with a 0.6 M aqueous sodium hydroxide solution (i.e., under swelling conditions) and subsequently rinsed for 3×10 minutes with a 0.5 M aqueous sodium hydroxide solution. The membrane obtained was treated (i.e., crosslinked) for 30 minutes at room temperature with 30% 1,4-butanediol diglycidyl ether in a 0.1 M aqueous sodium hydroxide solution and 0.1% aqueous sodium borohydride solution, and then the moist membrane was left to stand for 20 hours in a closed vessel at room temperature.

Finally, it was rinsed for 30 minutes with running water.

The water flow rate of the activatingly crosslinked intermediate product was 45 ml/(min×bar×cm$^2$), and the degree of swelling was 16.2.

Example 3

Activatingly Crosslinked Intermediate Product for an Adsorption Membrane According to the Invention: Pretreatment of the Ca Membrane A CA membrane was treated in the same way as in example 2, with the exception that the CA membrane was heated for 20 minutes at 80° C. in the drying cabinet prior to the hydrolysis.

The water flow rate of the resulting activatingly crosslinked intermediate product was 21 ml/(min×bar×cm$^2$), and the degree of swelling was 34.8.

Example 4

Activatingly Crosslinked Intermediate Product for an Adsorption Membrane According to the Invention Pretreatment of the CA Membrane A CA membrane was treated in the same way as in example 2, with the exception that the CA membrane, prior to the hydrolysis, was heated in a 20% acetic acid solution to 80° C. and rinsed for 15 minutes with running water.

The water flow rate of the resulting activatingly crosslinked intermediate product was 180 ml/(min×bar×cm$^2$), and the degree of swelling was 4.06.

Example 5

Various Alkali Hydroxides

CA membranes were, in each case, hydrolyzed in 0.5 M aqueous solutions of LiOH, NaOH, and KOH for 30 minutes at room temperature, and subsequently, without rinsing, crosslinked for 3.5 hours at room temperature with aqueous solutions of 15% 1,4-butanediol diglycidyl ether and 0.1% sodium borohydride solution in the same alkali metal hydroxide solutions. The membranes were further reacted with a quaternary ammonium ligand by treating the crosslinked membranes for 35 minutes at 30° C. in a 10% aqueous solution of trimethylamine and for 5 minutes at room temperature in a 5% sulfuric acid solution and then rinsing them for 10 minutes with running water. The results are reported in table 3.

Example 6

Nonactivatingly Crosslinked Intermediate Product for Adsorption Membrane According to the Invention A CA membrane, as in example 1, was used as a starting membrane. This CA membrane was hydrolyzed for 30 minutes at room temperature with a 0.6 M aqueous sodium hydroxide solution and subsequently rinsed for 3×10 minutes with a 0.5 M aqueous sodium hydroxide solution. The membrane obtained was treated (crosslinked) for 30 minutes at room temperature with aqueous 15% 1,4-butanediol diglycidyl ether in a 0.5 M aqueous sodium hydroxide solution and 0.1% aqueous sodium borohydride solution, and then the moist membrane was left to stand for 20 hours in a closed vessel at room temperature. Finally, it was rinsed for 30 minutes with running water.

The water flow rate of the nonactivatingly crosslinked intermediate product was 31 ml/(min×bar×cm$^2$), and the degree of swelling was 23.5.

Example 7

Introduction of Quaternary Ammonium Ligands

Q Membrane

Activatingly crosslinked membranes (intermediate products) were treated for 35 minutes at 30° C. in a 10% aqueous solution of trimethylamine and for 5 minutes at room temperature in a 5% sulfuric acid solution and then rinsed for 10 minutes with running water, to obtain membranes having quaternary ammonium ligands (hereinafter: Q membranes).

Example 8

Introduction of Sulfonic Acid Ligands

S Membrane

Activatingly crosslinked membranes (intermediate products) were treated for 45 minutes at 80° C. in an aqueous solution of 30% sodium sulfite and 2.5% Na$_2$HPO$_4$×H$_2$O at a pH of 8.0 and then rinsed for 10 minutes with running water, for 5 minutes with 35 g of a 1% HCl solution, for 2×5 minutes with 35 g each time of an aqueous 1 M NaCl solution, for 5 minutes with 500 g of a 5% H$_2$SO$_4$ solution, and for 10 minutes with running water, to obtain membranes having sulfonic acid ligands (S membranes).

Example 9

Introduction of Iminodiacetic Acid Ligands

IDA Membrane

Activatingly crosslinked membranes (intermediate products) were treated for 45 minutes at 80° C. with a 13% aqueous solution of iminodiacetic acid at a pH of 11.2 and then rinsed for 10 minutes with running water, for 5 minutes with a 1% HCl solution, for 2×5 minutes with an aqueous 1 M NaCl solution, and for 10 minutes with running water, to obtain membranes having iminodiacetic acid ligands (IDA membranes).

Example 10

Introduction of Phenyl Ligands

Ph Membrane

Activatingly crosslinked membranes (intermediate products) were treated for three hours at room temperature with an aqueous solution of 1% aniline in a 0.1 M potassium phosphate (KPi) buffer at a pH of 8.0, and the moist samples were left for 19 hours in a sealed vessel. 15 minutes of rinsing with running water were followed by rinsing for 15 minutes with a 1 M aqueous NaCl solution and for 15 minutes with running water, to obtain membranes having phenyl ligands (Ph membranes).

Example 11

Introduction of p-aminobenzamidine Ligands pABA Membrane

A nonactivatingly crosslinked cellulose hydrate membrane (intermediate product) according to example 6 was activated by a 30-minute treatment with a 1% aqueous solution of sodium periodate at room temperature, rinsed for 15 minutes with running water, treated for one hour at room temperature with a solution, adjusted to a pH of 5.6, of
4.3 g of p-aminobenzamidine dihydrochloride,
2.17 g of sodium cyanoborohydride,
2 g of a 1 M sodium hydroxide solution, and 34.8 g of McIlvaine buffer having a pH of 5.6 (mixture of 0.1 M citric acid monohydrate (Riedel-de-Haen cat. 33114) and 0.2 M disodium hydrogen phosphate dihydrate (Merck cat. 1.06580). Dissolve 21 g of citric acid monohydrate in 1 l of reverse-osmosis water (ROW)=0.1 M. Dissolve 35.6 g of disodium hydrogen phosphate dihydrate in 1 l of ROW=0.2 M. Introduce 500 g of 0.2 M disodium hydrogen phosphate dihydrate, and adjust pH to 5.6 with 0.1 M citric acid monohydrate), rinsed for 15 minutes with running water, treated in succession with 100 g of a 1% aqueous $NaBH_4$ solution and 100 g of a 1 M aqueous NaCl solution, and rinsed again for 15 minutes with running water. As a result, membranes having p-aminobenzamidine ligands (pABA membranes) were obtained.

Example 12

Introduction of Cibacron Blue 3GA Ligands

CB Membrane

A nonactivatingly crosslinked cellulose hydrate membrane (intermediate product) according to example 6 was treated for 24 hours at room temperature with a solution produced by admixing a 2% aqueous Cibacron Blue 3GA dye solution which has been stirred for 10 minutes at 80° C. and admixed at room temperature with a 3% aqueous sodium hydroxide solution, and rinsed successively for 60 minutes with running water, four times, for thirty minutes each time, with water at 80° C., and for 15 minutes with running water. As a result, membranes having Cibacron Blue 3GA ligands (CB membranes) were obtained.

Example 13

Drying of the Adsorption Membrane According to the Invention

CA membranes were hydrolyzed in a 0.5 M aqueous sodium hydroxide solution for 30 minutes at room temperature, subsequently, without rinsing, crosslinked with a solution of 30% 1,4-butanediol diglycidyl ether and 0.1% sodium borohydride in a 0.5 M aqueous sodium hydroxide solution at room temperature for 2.5 hours, then derivatized with trimethylamine, and tested with regard to their static binding capacity both in an undried state and in a dried state, having been dried at 80° C. in a circulating air drying cabinet. The results are reported in table 3.

Example 14

Determination of the Fraction of Ultrapores of the Entire Pore Volume of the Membranes To determine the fraction of ultrapores of the entire pore volume of the membranes, the CA membrane was hydrolyzed analogously to example 2 at different sodium hydroxide solution concentrations, rinsed with 0.5 M 5 NaOH, crosslinked as in example 2, and modified with sulfonic acid ligands as in example 8 (membranes 1-6). For comparison, the membrane from example 1 (membrane A) and the microfiltration membranes, known in the prior art, from Sartorius Stedim Biotech GmbH having pore sizes in the range 0.2-0.45 µm (membranes B-F) were used.

The Blue Dextran used was commercially available dextran from Leuconostoc mesenteroides, strain B 512, modified with Reactive Blue 2 dye, about 0.1 mmol of Reactive Blue 2 per gram of dextran (Blue Dextran Molecular Weight (Mw) 2 000 000 from Sigma, St. Louis, Mo., USA, product number D 5751, CAS number: 87915-38-6).

The hydrodynamic diameter d of this Blue Dextran can be calculated with the help of the Mark-Houwink-Sakurada equation:

$$d\ [nm]=0.054 \times Mw^{0.5}$$

and is 76.4 nm.

Ultrapores are, as defined above, pores which are not accessible to Blue Dextran.

The pore volume accessible to water is referred to as Vw [$cm^3$]. It is assumed that all membrane pores are accessible to water, and therefore Vw corresponds to the entire pore volume of the membrane.

The pore volume accessible to Blue Dextran is referred to as Vd [$cm^3$].

The pore volume of the ultrapores which is not accessible to Blue Dextran is referred to as Vp [$cm^3$].

Vp is increased by the method according to the invention, in which the cellulose ester membrane swells during the hydrolysis.

The following equations apply: Vw=Vd+Vp and Vp=Vw−Vd

The percentage of pores inaccessible to Blue Dextran in the membrane is % Vp=100×(Vw−Vd)/Vw.

The pore volume Vd accessible to Blue Dextran is determined by the following method:

10 ml of a solution of Blue Dextran in RO water of a known concentration (c0) are filtered through a wet membrane. As a result, the water from the pore volume accessible to Blue Dextran is replaced with the Blue Dextran solution. The prerequisite for the technique is that the membrane does not adsorptively bind the Blue Dextran. This is the case for unmodified cellulose hydrate membranes, crosslinked and uncrosslinked. A membrane having a diameter of 50 mm (i.e., an area of 19.6 $cm^2$) is intensively washed for 15 minutes with running RO water. The wet membrane is then incorporated into a filtration housing, and 10 ml of Blue Dextran solution having a concentration of 5 mg/ml (c0) are filtered through the membrane at a pressure of 0.1 bar. The membrane is then removed from the filtration housing, a section having a diameter of 47 mm (i.e., an area of 17.3 $cm^2$) is punched out of the middle (in order to remove the sealed edges of the membrane) and dabbed dry with a laboratory towel (Kimtech Science, 200, 2, 21×20 cm, white, 7101).

Afterwards, the membrane is shaken in an exactly determined amount (volume V=5.0 ml) of RO water in a sealed vessel for 20 hours at 80 rpm. The concentration of the Blue Dextran solution (c) is then determined photometrically at 618 nm. The extinction coefficient E (1 mg/ml; 1 cm) of the Blue Dextran solution is 0.896. From the concentration of the Blue Dextran solution, the pore volume accessible to Blue Dextran is calculated:

$$Vd\ [cm^3]=c \times V/c0$$

The pore volume accessible to water is determined by the following method:

The membrane sample is intensively washed for 15 minutes with running RO water. The water adhering to the membrane is dabbed off with the laboratory towel, and the wet membrane is weighed. Afterwards, the membrane is dried at 80° C. in a circulating air drying cabinet for 30 minutes, and the dried membrane is weighed. The weight difference between the wet membrane and dry membrane corresponds to the amount of water in the membrane (Vw). A water density of 1.0 $g/cm^3$ is assumed.

From % $Vp=100 \times (Vw-Vd)/Vw$ the percentage of the pore volume not accessible to Blue Dextran in the entire pore volume is calculated.

With increasing sodium hydroxide solution concentration in the hydrolysis of the cellulose acetate membrane, the swelling becomes stronger, the degree of swelling increases, the permeability of the membrane decreases, the membrane thickness increases, the fraction of ultrapores of the entire pore volume increases, and the binding capacity increases, as is apparent from table 1 below.

TABLE 1

| | Hydrolysis $c$(NaOH) [M] | Rinsing after hydrolysis $c$(NaOH) [M] | Vp [%] | Permeability, 10 mM KPi, pH 7 S membrane [ml/(min × bar × cm$^2$)] | Binding capacity, lysozyme S membrane [mg/cm$^2$] | Degree of swelling [—] |
|---|---|---|---|---|---|---|
| 1 | 0.20 | 0.5 | 16% | 515 | 0.75 | 1.4 |
| 2 | 0.40 | 0.5 | 25% | 341 | 1.40 | 2.1 |
| 3 | 0.50 | 0.5 | 30% | 180 | 1.71 | 4.1 |
| 4 | 0.60 | 0.5 | 34% | 73 | 1.99 | 10.0 |
| 5 | 0.75 | 0.5 | 39% | 8 | 2.23 | 90.1 |
| 6 | 1.00 | 0.5 | 45% | 4 | 2.40 | 208.6 |

Example 15

Separation of Lysozyme and γ-Globulin in Phosphate Buffer Having pH 7.0

A mixture of lysozyme and γ-globulin was used as a model system for protein separation. Some parameters of the proteins used are as follows:
Lysozyme from chicken egg from SIGMA, ordering number L-6876/25G, lot 096K1237, having a MW of 14.3 kDa and an IP of 10.5;
γ-Globulin from bovine serum from SIGMA, ordering number G-5009/100G, lot 116K7011, having a MW of 150 kDa and an IP of 7-8.

Five layers of an S membrane from example 8 were clamped into a membrane holder. The membrane stack had a membrane area of 100 cm$^2$, an inflow area of 20 cm$^2$, and a bed height (thickness of the membrane stack) of 1.4 mm in the membrane holder. The membranes in the membrane holder were flooded with a 10 mM KPi buffer having a pH of 7.0 in order to displace the air and then connected to an Äkta Explorer 100 FPLC system from General Electric Health Care.

The mixture to be separated is a mixture of the above-described lysozyme and γ-globulin in a lysozyme:γ-globulin protein concentration ratio of 1.1:1 (0.37 mg/ml of lysozyme and 0.33 mg/ml of γ-globulin in a 10 mM KPi buffer having a pH of 7.0).

Afterwards, the membranes, i.e., the membrane stack, were tested with regard to the separation of the proteins with a test program comprising four steps. The four steps of the test program are specified below:
1. Equilibrating the membranes with 25 ml of the 10 mM KPi buffer having a pH of 7.0, which flows through the membranes at a flow rate of 5 ml/min,
2. Loading the membrane with 600 ml of the solution of 0.37 mg/ml lysozyme and 0.33 mg/ml γ-globulin in a 10 mM KPi buffer having a pH of 7.0 at a flow rate of 5 ml/min,
3. Washing the loaded membranes with 50 ml of a 10 mM KPi buffer having a pH of 7.0 at a flow rate of 10 ml/min, and
4. Eluting the loaded and washed membranes with 50 ml of 1 M NaCl in a 10 mM KPi buffer having a pH of 7.0 at a flow rate of 10 ml/min.

The liquid flowing through upon loading of the membrane stack (flow-through) was collected in fractions of 10 ml each. The concentrations of lysozyme and γ-globulin in the individual fractions were determined by means of GPC. For this purpose, an HPLC system, from DIONEX, having a P580 pump, an ASI-100 injector, an STH 585 column compartment, and a UVD 170U UV detector was used. The chromatography column used was a PSS Proteema 300 (8×300 mm) column from Polymer Standard Sciences. The flow rate was 1 ml/min in a 50 mM NaPi buffer in 0.3 M NaCl having a pH of 6.7 and a conductivity (Con) of 32 mS/cm. The injection volume was 0.1 ml, and the compartment temperature was 20° C. Cleaning of the column was carried out with a 50 mM NaPi buffer+0.05% sodium azide having a pH of 6.86 and a Con of 5.82 mS/cm.

From the chromatograms obtained, the respective amounts of lysozyme and γ-globulin were determined by comparison of the peak areas with the areas of known injection amounts of the proteins.

The amounts of lysozyme and γ-globulin determined by means of the individual GPC analyses were plotted against the respective fraction number. The resulting breakthrough curve is displayed in FIG. 6.

In this context, "breakthrough" means a rise in the protein concentration in the outflow of the membrane adsorber unit. The protein amount bound up to this time point was determined from the breakthrough curve.

Furthermore, the breakthrough curve was determined by detection of the absorbance, i.e., the optical density OD, at 280 nm. FIG. 7 displays the breakthrough curve obtained as the UV signal versus the loading.

FIG. 8 reports the GPC analysis of the starting solution of lysozyme and γ-globulin of example 15, i.e., lysozyme and γ-globulin in a protein concentration ratio of 1.1:1, viz. 0.37 mg/ml lysozyme and 0.33 mg/ml γ-globulin in a 10 mM KPi buffer having a pH of 7.0.

It is apparent from FIG. 9 of the GPC analysis of the fraction of the flow-through after a 400 ml loading that the lysozyme was completely removed from the first 400 ml of solution, whereas an immediate breakthrough of γ-globulin occurred. The breakthrough for lysozyme occurred only after a loading of more than 400 ml of solution (see FIG. 6). 148 mg of lysozyme were bound to the membrane after a loading of 400 ml of solution, corresponding to a dynamic binding capacity of 1.48 mg/cm$^2$ at 0% breakthrough.

From the GPC analysis of the elution fraction (diluted 1:10) displayed in FIG. 10, it is apparent that no γ-qlobulin was found in the elution fraction. For elution, the adsorber was loaded with a solution of 1 M of NaCl in the appropriate buffer until the UV signal of the flow rate photometer of the FPLC system had reached the base line again. The entire elutable protein amount was determined.

Example 16

Separation of Lysozyme and γ-globulin in Phosphate Buffer Having pH 7.0

The separation was carried out as in example 15, but with the following change: The loading in step 2 was done with 1200 ml of a solution of 0.07 mg/ml lysozyme and 0.77 mg/ml γ-globulin in a 10 mM KPi buffer having a pH of 7.0. In FIG. 11, the amounts of lysozyme and γ-globulin determined by means of the individual GPC analyses are plotted against the respective fraction number. The lysozyme was completely removed with a membrane area of 100 cm$^2$. 84 mg of lysozyme were bound to the membrane after a loading of 1200 ml. Similarly to example 15, γ-globulin was also not found in the elution fraction in example 16.

Example 17

Separation of Lysozyme and γ-Globulin in Acetate Buffer Having pH 5.0

The separation was carried out as in example 15, but with the following change: The loading in step 2 was done with 600 ml of a solution of 0.37 mg/ml lysozyme and 0.33 mg/ml γ-globulin in a 20 mM sodium acetate+50 mM NaCl buffer having a pH of 5.0.

In FIG. 12, the amounts of lysozyme and γ-globulin determined by means of the individual GPC analyses are plotted against the respective fraction number.

FIG. 13 displays the breakthrough curve for lysozyme and γ-globulin according to determination of the absorbance (optical density OD) at 280 nm, as the UV signal versus the loading.

An early breakthrough of lysozyme at a loading volume of about 350 ml can be observed. In the elution fraction, it was also not possible to detect here any γ-globulin by means of GPC analysis.

Example 18

Separation of Lysozyme and γ-Globulin in Phosphate Buffer Having pH 7.0

The separation was carried out as in example 15, but with the following change: The loading in step 2 was done at a flow rate of 20 ml/min with 600 ml of a solution of 0.43 mg/ml lysozyme and 0.39 mg/ml γ-globulin in a 10 mM KPi buffer having a pH of 7.0.

In FIG. 14, the amounts of lysozyme and γ-globulin determined by means of the individual GPC analyses are plotted against the respective fraction numbers.

FIG. 15 displays the breakthrough curve for lysozyme and γ-globulin according to determination of the absorbance (optical density OD) at 280 nm, as the UV signal versus the loading.

The result with regard to the separation is comparable with the result from example 15.

Comparative Example 1

Separation of Lysozyme and γ-Globulin in Phosphate Buffer Having pH 7.0

The separation was carried out as in example 18, but with the following change: Instead of the S membrane from example 8, a conventional Sartobind® S membrane from Sartorius Stedim Biotech GmbH was used.

In FIG. 16, the amounts of lysozyme and γ-globulin determined by means of the individual GPC analyses are plotted against the respective fraction numbers.

FIG. 17 displays the breakthrough curve for lysozyme and γ-globulin according to determination of the absorbance (optical density OD) at 280 nm, as the UV signal versus the loading.

The early breakthrough of lysozyme at about 150 ml loading is distinctly recognizable, and, in contrast to membranes according to the invention, γ-globulin was found in the elution fraction.

Table 2 below summarizes the measured values for the protein separation of lysozyme and γ-globulin under various operating conditions.

TABLE 2

| | | | | Starting solution | | Elution | |
|---|---|---|---|---|---|---|---|
| Example | Membrane | Buffer | Flow rate [ml/min] | Lysozyme [mg/ml] | γ-Globulin [mg/ml] | Lysozyme [mg/ml] | γ-Globulin [mg/ml] |
| 15 | Example 8 | KPi, pH 7.0 | 5 | 0.37 | 0.33 | 3.10 | n.a.[1] |
| 16 | Example 8 | KPi, pH 7.0 | 5 | 0.07 | 0.77 | 1.93 | n.a. |
| 17 | Example 8 | Acetate, pH 5.0 | 5 | 0.37 | 0.33 | 2.37 | n.a. |
| 18 | Example 8 | KPi, pH 7.0 | 20 | 0.43 | 0.39 | 3.29 | n.a. |
| Comparative example 1 | Sartobind ® S | KPi, pH 7.0 | 20 | 0.43 | 0.39 | 1.76 | 0.127 |

[1] n.a. means "not detectable"

The results of the determination of the static binding capacities for lysozyme and γ-globulin and their separation show that the membranes according to the invention have distinctly higher selectivities and improved separation properties compared with the membranes known in the prior art.

Through the combination of the adsorptive interaction of the adsorbate with the membrane and of the size-exclusion effect of the membrane, it is possible to achieve an improved separation. The membranes according to the invention can be used in the fast separation of biomolecules of different sizes but with similar adsorptive properties (e.g., identically charged molecules on an oppositely charged membrane according to the invention).

Evaluation of the Membranes

The membranes obtained were evaluated in the manner described below:

1) Flow Rate Determination

Membranes having an active membrane area of 12.5 cm$^2$ were each incorporated into a housing, and the time taken for the filtration of 100 ml of water or buffer was measured. The flow rate figures reported in table 3 for membranes reacted with functional groups relate to the corresponding binding buffer. The same buffers were used as for the determination of the binding capacities described below.

2) Determining the Static Binding Capacity of Q Membranes

Membrane samples having, in each case, an active membrane area of 17.6 cm² were shaken in 35 ml of 20 mM Tris/HCl, pH 7.3, for 3×5 minutes at about 80 revolutions per minute (rpm). Afterwards, the membrane samples were shaken in 35 ml of a solution of 2 mg/ml bovin serum albumin (BSA) solution in 20 mM Tris/HCl, pH 7.3 for 12-18 hours at 20-25° C. at about 80 rpm. Subsequently, the membrane samples were rinsed for 2×15 minutes in, in each case, 35 ml of 20 mM Tris/HCl, pH 7.3. Afterwards, the membrane samples were shaken in 20 ml of 20 mM Tris/HCl, pH 7.3+1 M aqueous NaCl solution. The amount of the eluted protein was determined by measurement of the optical density (OD) at 280 nm.

3) Determining the Static Binding Capacity of S Membranes

Membrane samples having, in each case, an active membrane area of 17.6 cm² were shaken in 35 ml of 10 mM KPi, pH 7.0, for 3×5 minutes at about 80 rpm. Afterwards, the membrane samples were shaken in 35 ml of a solution of 2 mg/ml lysozyme or 1 mg/ml γ-globulin in binding buffer for 12-18 hours at 20-25° C. at about 80 rpm. Subsequently, the membrane samples were rinsed for 2×15 minutes in, in each case, 35 ml of binding buffer. Afterwards, the membrane samples were shaken in 20 ml of 10 mM KPi, pH 7.0+1 M aqueous NaCl solution. The amount of the eluted protein was determined by measurement of the optical density (OD) at 280 nm.

4) Determining the Static Binding Capacity of IDA Membranes

Membrane samples having an active membrane area of 17.6 cm² were shaken in 35 ml of 10 mM KPi, pH 7.0, for 3×5 minutes at about 80 rpm. Afterwards, the membrane samples were shaken in 35 ml of a solution of 2 mg/ml lysozyme in 10 mM KPi, pH 7.0 for 12-18 hours at 20-25° C. at about 80 rpm. Subsequently, the membrane samples were rinsed for 2×15 minutes in, in each case, 35 ml of 10 mM KPi, pH 7.0. Afterwards, the membrane samples were shaken in 20 ml of 10 mM KPi, pH 7.0+1 M aqueous NaCl solution. The amount of the eluted protein was determined by measurement of the optical den-sity (OD) at 280 nm.

5) Determining the Static Binding Capacity of Metal Chelate Membranes (Iminodiacetic Acid Ligand (IDA) Complexed with $Cu^{2+}$ Cations)

IDA membrane samples having an active membrane area of 3.1 cm² were clamped into a polycarbonate attachment and connected to a peristaltic pump. 10 ml of each solution were pumped in the following order through the membranes with the help of the peristaltic pump at a flow rate of 2

1. 0.1 M $CH_3COONa$+0.5 M NaCl, pH 4.5
2. 0.1 M $CH_3COONa$+0.5 M NaCl, pH 4.5+0.1 M $CuSO_4$
3. 0.1 M $CH_3COONa$+0.5 M NaCl, pH 4.5
4. 0.05 M KPi+0.5 M NaCl, pH 7.5
5. 2 mg/ml cytochrome C in 0.05 M KPi+0.5 M NaCl, pH 7.5
6. 0.05 M KPi+0.5 M NaCl, pH 7.5
7. 0.1 M imidazole in 0.05 M KPi+0.5 M NaCl, pH 7.5
8. 1 M $H_2SO_4$ The amount of the eluted protein in step 7 was determined by measurement of the optical density (OD) at 528 nm.

6) Determining the Static Binding Capacity of Ph Membranes

Membrane samples having an active membrane area of 3.1 cm² were clamped into a polycarbonate attachment and connected to a peristaltic pump. Solutions were pumped in the following order through the membranes with the help of the peristaltic pump at a flow rate of 2 ml/min:

1. 10 ml of 0.05 M KPi+1 M $(NH_4)_2SO_4$NaCl, pH 7.0
2. 20 ml of 1 mg/ml gamma-globulin in 0.05 M KPi+1 M $(NH_4)_2SO_4$NaCl, pH 7.0
3. 20 ml of 0.05 M KPi+1 M $(NH_4)_2SO_4$NaCl, pH 7.0
4. 10 ml of 0.05 M KPi, pH 7.0

The amount of the eluted protein in step 4 was determined by measurement of the optical density (OD) at 280 nm.

7) Determining the Static Binding Capacity of pABA Membranes

Membrane samples having an active membrane area of 3.1 cm² were clamped into a polycarbonate attachment and connected to a peristaltic pump. Solutions were pumped in the following order through the membranes with the help of the peristaltic pump at a flow rate of 2 ml/min:

1. 10 ml of 50 mM Tris/HCl, pH 8.8+10 mM $CaCl_2$+250 mM NaCl
2. 10 ml of 2 mg/ml trypsin type I in 50 mM Tris/HCl, pH 8.8+10 mM $CaCl_2$+250 mM NaCl
3. 10 ml of 50 mM Tris/HCl, pH 8.8+10 mM $CaCl_2$+250 mM NaCl
4. 10 ml of 0.1 M glycine/HCl, pH 2.8

The amount of the eluted trypsin in step 4 was determined by trypsin determination as described by Bergmeyer by the following method. The enzymatic activity of trypsin is determined as ΔA/min through the change in absorbance of N-α-benzoyl-L-arginine ethyl ester hydrochloride (BAEE) at a wavelength of 253 nm in the hydrolysis catalyzed by trypsin.

In a semi-micro quartz cuvette, the following solutions are mixed in the specified order:

1. 850 µl of buffer (50 mM Tris/HCl, pH 8.8+10 mM $CaCl_2$+250 mM NaCl),
2. 100 µl of BAEE solution in binding buffer (Sigma cat. no. B 4500), and
3. 50 µl of sample.

The filled cuvette is placed in a photometer, and ΔA/min is determined at 253 nm after 5 seconds.

8) Determining the Static Binding Capacity of CB Membranes

Membrane samples having an active membrane area of 9.8 cm² were shaken in 10 ml of a 0.1 M aqueous sodium hydroxide solution for 10 minutes and then shaken in 10 ml of 10 mM KPi, pH 7.3, for 3×10 minutes at about 80 rpm. Afterwards, the membrane samples were shaken in 5 ml of a solution of 2 mg/ml bovine serum albumin (BSA) in 10 mM KPi, pH 7.0 for 12-18 hours at 20-35° C. at about 80 rpm. Subsequently, the membrane samples were rinsed for 3×10 minutes in, in each case, 10 ml of 10 mM KPi, pH 7.0. Afterwards, the membrane samples were shaken for one hour in 5 ml of 10 Mm KPi, pH 7.0+1 M aqueous NaCl solution. The amount of the eluted protein was determined by measurement of the optical density (OD) at 280 nm.

9) Confocal Laser Scanning Microscopy

Labeling the Membranes

An adsorption membrane from example 1 and an adsorption membrane according to the invention as per example 2 were provided with sulfonic acid ligands according to example 8. Together with an adsorption membrane from Sartorius Stedim Biotech GmbH, commercially available under the trade name Sartobind® S, having a sulfonic-acid-overlaid auxiliary polymer, the membranes were labeled with the OH-reactive fluorescent dye "5-DTAF" (5-(4,6-dichlorotriazinyl) aminofluorescein, excitation wavelength and emission wavelength of 492 nm and 516 nm, respectively Invitrogen). The incubation of the solution of the dye and also all following wash steps were carried out with, in each case, three membrane samples (diameter: 13 mm) in a filter holder with continuous rinsing at a flow rate of about 1 ml/min. Use was made, in each case, of 20 ml of a 5-DTAF solution in a 100 mM sodium hydrogen carbonate solution having a pH of 9.3 and having concentrations matched to the membrane, viz. 13.5 µg/ml 5-DTAF+100 mM NaCl solution for the membranes according to examples 1 and 2, and 25 µg/ml 5-DTAF+ 200 mM NaCl solution for the Sartobind® S membrane. Since it was suspected that the three-dimensional cation exchanger layer causes particularly effective shielding of the cellulose matrix, both the dye concentration and the salt concentration were increased for the Sartobind® S membrane. After rinsing for about 18 hours, the samples were subsequently washed in succession with, in each case, 100 ml of a 20% ethanol solution, a 1 M NaCl solution, and a 200 mM sodium phosphate buffer, pH 7.0. For the CLSM analysis, the second sample in the filter holder was used in each case because it had the best homogeneity of labeling.

Labeling and Cleanup of the Protein

Lysozyme (available from Sigma, St. Louis, Mo., USA; protein about 95%, about 50 000 units/mg of protein) was labeled with the $NH_2$-reactive fluorescent dye "Cy5 mono-Reactive NHS Ester" (available from GE Health Care Bio-Sciences AB, Uppsala, Sweden) in a sodium carbonate buffer, pH 9.3, and also subsequently cleaned up, firstly by gel filtration and then by HP ion exchange chromatography. By appropriate selection of the chromatographic fractions, the singly labeled lysozyme was obtained in a pure form. Afterwards, concentration was effected by means of ultrafiltration, to the concentration necessary for the binding experiment. The concentration of the labeled lysozyme was determined by means of a UV-Vis photometer (measurement of the absorbances at 280 nm and 650 nm).

Incubating the Membranes with Protein

Samples of the membranes labeled with 5-DTAF were punched out with a diameter of 5 mm and incubated for four hours in a solution of the labeled lysozyme having a concentration of 0.6 g/L in a 200 mM sodium phosphate buffer, pH 7.0+50 mM aqueous NaCl solution (for 1 $cm^2$ samples, 4.1 ml of protein solution were used in each case). Afterwards, the samples were washed with the buffer for 15 minutes.

CLSM Analysis

The analysis was effected with the CLSM system Leica TCS SP. Each sample was examined in a 200 mM sodium phosphate buffer from both surfaces. First, a suitable signal amplification was determined (criteria: suppressed autofluorescence of the membrane; the maximum of the signal amplification was set with the help of the histogram in the evaluation software "Zeiss LSM Image Browser" in order to avoid local overexposure) and z=0 was identified (criteria: high scattering intensity and subsequent first identification of the pore morphology with further reduction of the distance to the sample). Afterwards, the characteristic morphology of the Sartobind® S membranes known from SEM was searched for in x,y-scans at different z-positions. Afterwards, detailed x,y-scans of the two excitation wavelengths (488 nm for 5-DTAF, 633 nm for Cy5) were carried out in a narrow range of different z-positions (at a depth of about 20 micrometers, at intervals of 1 micrometer in both directions). For each sample and each orientation, these scans were carried out, in each case, for three different positions. The Sartobind® S sample was analyzed first; the settings chosen for this sample (z-position and signal amplification) were retained for the analysis of the other membrane samples. Because the signal intensities of the membrane according to the invention as per example 2 were very much higher at 633 nm than for the other two membranes, a reduction of the signal amplification was made:

"Gains" (488 nm/633 nm)
Sartobind® S membrane: 426/643
Membrane according to example 1: 426/669
Membrane according to example 2: 357/650

CLSM Evaluation

The evaluations were carried out with the help of the Zeiss LSM Image Browser 3.5.0.376. From the images obtained, detailed x,y-scans in a range of the z-positions of a depth of about 20 µm for the upper side were selected. The images obtained were each displayed as 8-bit images having a resolution of 512×512 pixels, corresponding to 146.2×146.2 $µm^2$. FIGS. 2 to 4 show the overlapping of the two images of the distribution of lysozyme and of the pore morphology of the cellulose. Additionally, an intensity profile of the intensities for both fluorescent labels is also shown for each measurement at the upper right edge of the picture.

Results of the Experiments

The results of the experiments are shown in table 3 below.

TABLE 3

| Membrane from example | Remark | Ligand | Protein | Flow rate | Binding capacity |
|---|---|---|---|---|---|
| 1 | | Q | BSA | 643 | 0.07 |
| | | S | Lysozyme | 664 | 0.01 |
| | | IDA | Lysozyme | 681 | 0.03 |
| | | IDA + $Cu^{2+}$[1] | Cytochrome C | 681 | 0.15 |
| | | Ph | Gamma-globulin | 570 | 0.2 |
| 2 | | Q | BSA | 44 | 0.92 |
| | | S | Lysozyme | 38 | 2.06 |
| | | IDA | Lysozyme | 41 | 1.91 |
| | | IDA + $Cu^{2+}$[1] | Cytochrome C | 41 | 0.5 |
| | | Ph | Gamma-globulin | 31 | 1.26 |
| 3 | | Q | BSA | 20 | 1.13 |
| | | S | Lysozyme | 24 | 2.85 |
| 4 | | Q | BSA | 158 | 0.74 |
| | | S | Lysozyme | 167 | 3.11 |
| | | S | Gamma-globulin | 167 | 0.44 |
| 5 | LiOH | Q | BSA | 70 | 1.18 |
| | NaOH | Q | BSA | 109 | 0.93 |
| | KOH | Q | BSA | 519 | 0.08 |
| 6 | | CB | BSA | 30 | 0.31 |
| | | pABA | Trypsin | 35 | 0.75 |
| 13 | Undried | Q | BSA | 213 | 0.94 |
| | Dried | Q | BSA | 239 | 0.92 |

[1]Metal chelate of iminodiacetic acid ligand (IDA) complexed with $Cu^{2+}$ cations.

Comparative Example 2

Simultaneous hydrolysis and crosslinking as in example 1, sample K10C of WO 2007/017085 A2, but with 1,4-butanediol diglycidyl ether instead of epichlorohydrin, under non-swelling conditions.

A CA membrane as defined above and a 0.65 µm cellulose acetate membrane as in example 1, sample K10C of WO 2007/017085 A2 having a water flow rate of 65 ml/(min×bar× $cm^2$) were used as starting membranes.

The cellulose acetate membranes were heated to 47° C. in 100 g of water, 10 g of $Na_2SO_4$, and 1 g of 1,4-butanediol diglycidyl ether, and 10 g of a 1 M aqueous sodium hydroxide solution were metered in over 30 minutes. The membranes were further treated in the solution for 3.5 hours at 47° C. and subsequently rinsed for 30 minutes with running water. Quaternary ammonium ligands were introduced into the membranes to obtain Q membranes. The hydrolyzed and crosslinked Q membrane obtained from the CA membrane exhibited a water flow rate of 589 ml/(min×bar×$cm^2$), a degree of swelling of 1.2, and a binding capacity for BSA of 0.04 mg/cm². The hydrolyzed and crosslinked Q membrane obtained from the cellulose acetate membrane according to example 1, sample K10C of WO 2007/017085 A2 exhibited a water flow rate of 66 ml/(min×bar×cm²), a degree of swelling of 1.0, and a binding capacity for BSA of 0.04 mg/cm².

Comparative Example 3

Attempt to Swell Previously Hydrolyzed Cellulose Hydrate Membranes

A CA membrane as defined above and used as a starting membrane was hydrolyzed for three minutes at room temperature with a 15% potassium hydroxide solution in 80% ethanol and subsequently rinsed for three minutes with a 6.8% acetic acid solution, twice with ethanol, and for 15 minutes with running RO water. The hydrolyzed membrane obtained was treated for 30 minutes at room temperature with a 0.6 M aqueous sodium hydroxide solution and then rinsed three times for 10 minutes with a 0.5 M aqueous sodium hydroxide solution. Subsequently, the membrane was treated for 30 minutes at room temperature with a 30% solution of 1,4-butanediol diglycidyl ether in a 0.1 M aqueous sodium hydroxide solution and 0.1% aqueous sodium borohydride solution, whereupon the moist membrane was left to stand for 20 hours in a closed vessel at room temperature. Finally, the membrane obtained was rinsed for 30 minutes with running water.

The water flow rate of the hydrolyzed and crosslinked cellulose hydrate membrane thus produced was 688 ml/(min×bar×cm²), and the degree of swelling was 1.06.

Quaternary ammonium ligands or sulfonic acid ligands were, as described in example 7 or 8, introduced into two samples of the membrane to obtain a Q membrane and an S membrane. The Q membrane exhibited a binding capacity for BSA of 0.044 mg/cm², and the S membrane exhibited a binding capacity for lysozyme of 0.067 mg/cm².

What is claimed is:

1. A method for separating a mixture of materials comprising at least two components of different average molecular weight Mw in a range from 4000 to 4 000 000, comprising the steps:
    A) contacting the mixture of materials in a first liquid medium with at least one flat adsorbent and adsorptively depleting the at least one component having a lower average molecular weight from the first liquid medium through the at least one flat adsorbent, and
    B) separating the at least one flat adsorbent from step A) from the first liquid medium, which comprises the at least one component having a higher average molecular weight,
        wherein the at least one flat adsorbent is a membrane having a porous double structure consisting of:
        micropores having a diameter in the range from >100 nm to 20 μm, and
        ultrapores which have a diameter of <100 nm and which are not accessible to Blue Dextran having an average molecular weight Mw of 2 000 000, and
    wherein a fraction of the volume of the ultrapores is more than 15% of an entire pore volume accessible to water, and
    wherein the membrane is obtained by a method comprising:
        providing a cellulose ester membrane as a starting material for the membrane; and
        sequentially hydrolyzing said cellulose ester membrane in a swelling medium and crosslinking said cellulose ester membrane with an at least bifunctional agent, wherein the duration of hydrolysis is in the range of 5 to 45 minutes.

2. The method as claimed in claim 1, wherein the following steps follow step B):
    C) contacting the flat adsorbent from step B) with at least one second liquid medium with desorption of at least one component of the mixture of materials comprising at least two components, and
    D) separating the at least one flat adsorbent from step C) from the second liquid medium from step C).

3. The method as claimed in claim 1, wherein the micropores stretch from a first main surface of the membrane through the membrane to a second main surface and are connected with the formation of channels communicating with one another, and the ultrapores stretch from an inner surface of the micropores into a material forming the structure of the membrane, forming a dead end, and/or connect neighboring micropores with one another.

4. The method as claimed in claim 1, wherein one or more functional groups are bonded to the membrane.

5. The method as claimed in claim 4, wherein the functional groups are ligands which are capable of entering into interactions with adsorbates present in media.

6. The method as claimed in claim 5, wherein the ligands comprise anionic and/or cationic groups.

7. The method as claimed in claim 6, wherein the cationic groups are selected from the group consisting of primary, secondary, tertiary, and/or quaternary amines.

8. The method as claimed in claim 6, wherein the anionic groups are selected from the group consisting of sulfonic acids, phosphoric acids, and carboxylic acids.

9. The method as claimed in claim 5, wherein the ligands are affinity ligands.

10. The method as claimed in claim 9, wherein the affinity ligands are selected from the group consisting of benzamidines, biomimetic ligands, and/or proteins.

11. The method as claimed in claim 5, wherein the ligands are selected from the group consisting of metal chelates.

12. The method as claimed in claim 5, wherein the ligands are selected from the group consisting of hydrophobic ligands.

13. The method as claimed in claim 5, wherein the ligands are selected from $C_1$-$C_{20}$-alkyl and their derivatives or $C_6$-$C_{25}$-aryl and their derivatives or $C_7$-$C_{25}$-arylalkyl and their derivatives or —[(CH$_2$)$_m$—O-]$_n$—R, where m is 2 or 3, n is a whole number greater than or equal to 1, and R is —H or —C$_1$-C$_5$-alkyl.

14. The method as claimed in claim 5, wherein the ligands are selected from the group consisting of reactive epoxide, aldehyde, azlactone, N-hydroxysuccinimide, and carbodiimide groups.

15. The method as claimed in claim 5, wherein the ligand is a catalyst.

16. The method as claimed in claim 5, wherein at least two structurally different ligands are bonded to the membrane.

17. The method as claimed in claim 1, wherein the membrane consists of at least one polysaccharide.

18. The method as claimed in claim 17, wherein the polysaccharide is cellulose.

19. The method as claimed in claim 2, wherein the separation of the at least one flat adsorbent from the second liquid medium is achieved by pressure filtration, vacuum filtration, centrifugation, or influence of gravity.

20. The method as claimed in claim 1, wherein the component having a higher average molecular weight has an average molecular weight of at least 50 000.

21. The method as claimed in claim 1, wherein the component having a higher average molecular weight has an average molecular weight of at least 100 000.

22. The method as claimed in claim 1, wherein the component having a higher average molecular weight is an antibody or an aggregate thereof.

23. The method as claimed in claim 1, wherein the component having a higher average molecular weight is a virus.

* * * * *

UNITED STATES PATENT AND TRADEMARK OFFICE
CERTIFICATE OF CORRECTION

PATENT NO. : 8,945,389 B2
APPLICATION NO. : 12/937899
DATED : February 3, 2015
INVENTOR(S) : René Faber et al.

Page 1 of 1

It is certified that error appears in the above-identified patent and that said Letters Patent is hereby corrected as shown below:

In the specification

In column 17 at line 58, Change "5 NaOH," to --NaOH,--.

In column 18 at line 64 (approx.), Change "(Vw-Vd)/Nw" to --(Vw-Vd)/Vw--.

In column 20 at line 62 (approx.), Change "v-qlobulin" to --γ-globulin--.

In column 23 at line 10 (approx.), Change "bovin" to --bovine--.

In column 23 at line 45, Change "den-sity" to --density--.

In column 23 at line 53, After "2" insert --ml/min:--.

In column 24 at line 27, Change "AA/min" to --ΔA/min--.

In column 24 at line 51, Change "Mm" to --mM--.

In the claims

In column 28 at line 51, In Claim 14, change "and" to --and/or--.

Signed and Sealed this
Ninth Day of February, 2016

Michelle K. Lee
*Director of the United States Patent and Trademark Office*